United States Patent [19]
Bechtel et al.

[11] Patent Number: 5,394,097
[45] Date of Patent: Feb. 28, 1995

[54] DIELECTRIC SENSOR

[76] Inventors: Friend K. Bechtel, 1523 Borah, Moscow, Id. 83843; James R. Allen, NE. 1165 Lybecker Rd.; Daniel A. Uskoski, NW. 750 Fisk, both of Pullman, Wash. 99163

[21] Appl. No.: 982,079
[22] Filed: Nov. 24, 1992
[51] Int. Cl.$^6$ .......................................... G01R 27/26
[52] U.S. Cl. .................... 324/687; 324/688; 324/684; 324/631; 324/663; 73/159
[58] Field of Search ................ 364/550; 324/683, 669, 324/684, 688, 686, 687, 690; 73/159

[56] References Cited

U.S. PATENT DOCUMENTS 3,196,672 7/1965 Keller .
3,805,156 4/1974 Norton .
4,201,093 5/1980 Logan .
4,926,350 5/1990 Bechtel .............................. 364/550
4,972,154 11/1990 Bechtel .

OTHER PUBLICATIONS

Bechtel et al: "Model 520 Grain Angle Indicator'—Technical Report—Jan. 17, 1992.
Bechtel et al: "Methods of Implementing Grain Angle Measurement . . . " Testing of Wood Symposium–Sep. 1987.
James: "Dielectric Properties of Wood . . . "–USDA Forest Service Research Paper Nr. FPL245-1975.
Fu: "Recent Developments in Pattern Recognition'—IEEE Trans. on Computers—Oct. 1980–pp. 845-854.

Primary Examiner—Kenneth A. Wieder
Assistant Examiner—Jose M. Solis

[57] ABSTRACT

Method and apparatus are described for obtaining information about the real and imaginary parts of permittivity in dielectric materials and relating this information to other properties of the materials.

20 Claims, 12 Drawing Sheets

DIELECTRIC SENSOR

TECHNICAL FIELD

This invention relates to methods and apparatus for obtaining measures of electrical properties of dielectric materials, most particularly wood, and relating these measures to other properties of the materials.

BACKGROUND OF THE INVENTION

Importance of the Invention and Prior Art

The electrical properties of dielectric materials that are of interest here include permittivity, measure of energy loss, direction of maximum permittivity, direction of maximum energy loss, and amounts of anisotropy both in permittivity and in energy loss. The dielectric sensor allows these electrical properties to be explored with different probing signals and used in the estimation of other properties of the material being measured. Although applications discussed in this disclosure are primarily to structural wood or wood products, the techniques are applicable to other dielectric materials.

In dielectric materials such as wood, there are a number of physical properties of interest. If the material is anisotropic, as is wood, these properties can be different along different directions, and the differences affect how the material can be used best. For example, in wood, bending modulus of elasticity (E) or stiffness and strength are functions of the direction of the wood fibers. When wood is used in structures, it is important that the structural properties are sufficient for the application. Strength is a structural property that cannot be measured nondestructively.

Present testing and sorting methods for wood are based on its visual appearance, nondestructive measurements of wood properties, or a combination of both. As well as being useful in estimating strength, measured properties can be important in their own right. For example, structural timber sold as machine stress rated lumber is measured and sorted for bending modulus of elasticity (E) in the longitudinal direction using technology described by Keller in U.S. Pat. No. 3,196,672. In this case E is used as an estimator for strength; but the E measure is itself useful in determining the rigidity of floor or other structural systems made of the tested product.

As another example of machine sorting of wood product, veneers used in laminated veneer lumber (LVL) are measured and sorted according to the propagation velocity of ultrasonic stress waves along a reference direction utilizing an invention by Logan in U.S. Pat. No. 4,201,093.

Industry acceptance of the Keller and Logan inventions in the form of production-line machines, the CLT Continuous Lumber Tester jointly produced by U.S. Natural Resources Inc. in Tigard, Oreg., and Metriguard Inc in Pullman, Wash., and the Model 2600 Veneer Grader produced by Metriguard Inc in Pullman, Wash., has demonstrated the value of machine sorting of wood product based on measurement or estimation of structural value. However, it is known that the present sorting methods for wood, although valuable, are still inadequate in accurately determining strength.

Wood can compete in strength with steel on a per unit weight basis. However, wood can be quite weak. The broad ranges of physical property values of wood and the present limited capability to sort based on these properties cause its structural design load values to be set relatively low for safety in its use. This means that the large bulk of wood which could be used safely at much higher loads is under-utilized and hence wasted.

Some aspects of wood which have been identified as contributing to its variable property values are the general direction of the wood fibers (grain angle), local deviation of grain angle such as occurs around knots, density, species, moisture content, orientation of growth rings with respect to machined wood surfaces and presence of juvenile or reaction wood.

The prior an by Norton et al in U.S. Pat. No. 3,805,156 and Bechtel et al in U.S. Pat. No. 4,972,154, describes how to measure grain angle in wood. Norton et al use a sensor with a rotating electric field, and Bechtel et al use a stationary sensor where one of the embodiments has two electric field patterns that are applied sequentially, first one and then the other during alternating time intervals. In either of these prior art technologies, the sensor has an operative surface in a sensor unit. During measurement, the operative surface is substantially parallel to a substantially plane (flat) surface of the material being measured.

In this disclosure, grain angle is the angle, relative to a reference direction, of the projection of the direction of an electrical property maximum onto a plane both parallel to a surface of the material being measured and including the reference direction. In the Norton et al and Bechtel et al prior art, the sensor unit outputs, from which grain angle is obtained, are determined by the direction of maximum permittivity.

Although grain angle in wood is important in the estimation of strength. (Bechtel and Allen 1987), grain angle by itself does not provide an indication of the amount of alignment. The question raised is not just in what direction are wood fibers preferentially aligned, but also, how well are they aligned? Additional questions can be asked. Is some wood better aligned than other wood? If one piece of wood is better aligned than, another, does it have greater strength? These questions can be asked both on a local scale and on a general scale.

Using a knot in wood as an example on a local scale, all the wood fibers about a knot are not aligned in the same direction; hence, a measure of the amount of alignment averaged over a sensed volume including the knot will not be as large as for a section of uniform straight-grained wood. A grain angle measurement using sensors of the type described in either U.S. Pat. Nos. 3,805,156 or 4,972,154 on a track along a piece of lumber going directly over a perfectly symmetrical knot will read zero grain angle at all points along the track. In this case, a measurement of grain angle alone misses the knot. The knot is missed because the sensed volume about points on the track before, over and past the knot have equal positive and negative contributions to grain angle, and these contributions average to zero just as they would if all the wood fibers were aligned in the zero direction. However, a measure of the amount of alignment is smaller in the vicinity of the knot than it is for the surrounding areas of uniform straight-grained wood and thus is useful in detecting and quantifying the knot.

As an example of reduced amount of alignment on a general scale, consider juvenile or reaction wood compared with normal mature wood. It is well known in the wood products industry that juvenile wood and reaction wood can have inferior structural value. According to Skaar 1988, speaking about longitudinal shrinkage: "This is believed to be the result of the difference between the fibril angles in the S2 layer in the cell walls of juvenile wood and those of mature wood" (Skaar, C., *Wood-Water Relations*, Springer-Verlag, New York, 1988). Skaar similarly describes reaction wood. We refer to the fibrils discussed by Skaar as microfibrils to distinguish them as constituents of wood fibers. From Skaar's description, these microfibrils spiral around the wood fibers with angle between microfibril direction and wood fiber direction being significantly greater for juvenile and reaction wood than for normal mature wood. Although the directions of the microfibrils, on the average, line up with the wood fiber direction, components of the microfibrils in directions transverse to the wood fiber direction are significantly greater for juvenile and reaction wood than for normal mature wood. Whereas a grain angle measurement measures zero grain angle so long as the juvenile or reaction wood fibers align with the zero reference direction, a measure of the mount of alignment can be less in this case than for normal mature wood because of the reduced longitudinal and increased transverse components of microfibril directions.

The increasing use of young trees has increased the amount of juvenile wood in the wood products industry. Development of equipment to detect and separate juvenile and reaction wood from demanding structural applications will have great value. Although the inventions of U.S. Pat. Nos. 3,805,156 and 4,972,154 are useful in measuring grain angle, those disclosures do not consider the problem of measuring the amount of alignment. The dielectric sensor of this invention, by providing a measure of the amount of anisotropy as an indicator for the amount of alignment, has promise for distinguishing juvenile and reaction wood from normal mature wood.

In some applications of wood, the orientation of the growth rings with respect to machined surfaces can be important. For example, the requirement of edge-grain wood is sometimes made for door framing, shingles and pencil slat material. The dielectric sensor of this invention has promise for detecting edge-grain versus non edge-grain material because of differences in electrical properties in the radial and tangential directions with respect to the growth rings in wood.

The present invention has application to reconstituted dielectric materials such as oriented flakeboard or fiberglass where the constituents (flakes or fibers) are formed together into a product having the fibers arranged preferentially in one direction. For process control or for sorting, it is desirable to have available a means for determining how well the material is aligned, that is, the amount of alignment. As will be seen, the dielectric sensor is useful in providing measures of the amount of alignment of these materials.

The amount of flake alignment in flakeboard is recognized as one of the most important variables in controlling the properties of flakeboard. There exists no other practical means of determining amount of flake alignment in the production line Methods previously considered have included measuring velocities of stress wave propagation or bending E in orthogonal directions and optical analysis of individual surface flakes. These approaches have been useful in the laboratory for off-line quality control and for research, but they have not been proved in the production-line.

The density of wood is also a variable of interest. Other measured properties being equal, greater density usually implies greater strength both of the wood itself and at the interface between wood and fasteners such as nail plates. However, this is not always true. Knots, for example, are a common strength reducing characteristic, and knots have higher density than the surrounding wood. The dielectric sensor of this invention has value because it can distinguish between high density well-aligned material and high density poorly-aligned material such as around knots in wood.

Moisture content is a confounding influence in both the measurement of electrical properties and density of wood. Moisture content increases the density, the conductivity and the permittivity of wood. Skaar 1988 discusses the increasing permittivity with increasing density (dry wood basis) at constant moisture content. Further, for relatively small moisture contents (below fiber saturation), it can be inferred from James 1975 and corroborated by our experiments that the amount of anisotropy in permittivity increases with moisture content (James, W.L., "Dielectric Properties of Wood and Hardboard: Variation with Temperature, Frequency, Moisture Content, and Grain Orientation," USDA Forest Products Lab Report FPL 245, 1975). Thus, estimates of moisture content can be made with the dielectric sensor. Moisture content is an important variable in many applications of wood. Other sensors for measuring moisture content are available, e.g. from Wagner Electronics Products in Rogue River, Oreg., but these sensors are not useful in measuring amount of anisotropy or grain angle.

Other sensors have been used to measure permittivity of dielectric materials in a set of different directions. For example, James 1975, describes apparatus he used to measure the permittivity of and energy loss in wood for each of its three principal directions, along the wood fibers, transverse to the fibers in the radial direction of the growth tings, and transverse to the fibers in the tangential direction of the growth rings. The measurements by James have provided the wood products industry with useful data about the electrical properties of wood. However, the equipment he used was designed to provide accurate laboratory data and was not intended to be used in the production-line where the constraints of measurement time, specimen preparation and orientation of the specimens with respect to the apparatus are completely different.

Brief Review of Former Patent

The present disclosure extends the apparatus and method of an earlier U.S. Pat. No. 4,972,154, herein called the "former patent". The former patent disclosed a new family of sensors for measuring grain angle in wood. Each sensor in the family of sensors included an array of electrodes separated into first and second electrode means. A general theory was developed which defined acceptable first and second electrode means. Electrodes in one of the electrode means (drive electrodes) were driven with time-varying electric potentials while electrodes in the other electrode means (sense electrodes) sensed potentials resulting from capacitive coupling through the wood and between drive and sense electrodes. The capacitive coupling changed as a function of grain angle of the wood according to the model $C=C_o+C_r\cos(2G-2M)$. In this model C is the capacitance between a pair of electrodes, $C_o$ is an isotropic component of C which is not dependent on probing angle, $C_v$ is the amplitude of a sinsoidally varying component of C caused by anisotropy in the material, G is the angle (grain angle) of the wood fibers as projected onto a plane surface of the wood, the angle measured relative to a reference direction in the plane surface, and M is the angle of the direction of the probing electric field relative to the reference direction.

A specific embodiment was described as the "division method". In the division method, time-varying electric potential signals are applied to the drive electrodes resulting in two sensed signals S1 and S2 which are proportional to $C_v\cos(2G)$ and $C_v\sin(2G)$. During a first time interval, the time-varying electric potential signals are defined so that the electric field probes in a direction coincident with the reference direction (M=O radians), resulting in the signal S1 which is proportional to $C_v\cos(2G)$. If the proportionality factor is $k_a$, then $S1=k_aC_v\cos(2G)$. During a second time interval, the time-varying electric potential signals are defined so that the resulting electric field probes in a direction 45 degrees from the reference direction (M=$\pi$/4 radians) resulting in the signal S2 which is proportional to $C_v\sin(2G)$. Provided conditions of measurement, other than probing direction, have not changed, the proportionality factor is $k_a$, and $S2=k_aC_v\sin(2G)$. Division of the second of these signals by the first, followed by an inverse tangent operation and scaling by ½ yields the grain angle G. Thus, $G=0.5 \tan^{-1} (S2/S1)$. This processing by division eliminates the amplitude factor $C_v$ and the proportionality factor $k_a$. By alternating between the first and second time intervals at a rate that is fast with respect to changes in the dielectric material being measured, the division method can keep up with changes in the material. The material can change, for example, if the material specimen being measured is moving rapidly past the electrodes.

A primary advantage of the technology disclosed by the former patent was the intrinsic cancellation of the effect of the isotropic component $C_o$ of capacitance that the electrode geometry and definition of drive signals provided. This was highly desirable for the sensors described in the former patent wherein the goal was measurement of grain angle.

Any dielectric material supporting and surrounding the electrodes also contributes to capacitive coupling between drive and sense electrodes. This capacitive coupling, which is not part of the specimen dielectric material to be tested, is referred to as background capacitance and denoted by $C_b$. If the dielectric material supporting and surrounding the electrodes is isotropic, then the effect of this background capacitance $C_b$ on measurements of grain angle is cancelled by the methods of the former patent.

The former patent has been implemented commercially as the Model 520 Grain Angle Indicator available from Metriguard Inc, Pullman, Wash.

SUMMARY OF THE PRESENT INVENTION

The dielectric sensor of the present invention obtains measures of the mount of anisotropy of an electrical property as well as the direction of maximum electrical property. Other advantages of the dielectric sensor will become apparent.

Sensing methods and apparatus for measuring dielectric material are described. Measures for any one or more of permittivity, energy loss, mount of anisotropy in permittivity, amount of anisotropy in energy loss, direction of maximum permittivity and direction of maximum energy loss are obtained. These measures, and in some cases information about other parameters such as bending E, wood temperature and distance between wood and sensor, can be used to derive estimates for grain angle, amount of alignment, moisture content, density, species, strength and orientation of growth rings with respect to machined wood surfaces. Additionally, sorting or classification into class categories by pattern recognition techniques can be performed.

The dielectric sensor of the present invention includes one or more sensor units, hereinafter called electrode units, each with an operative surface, an arrangement of electrodes in an electrode array and means for signal generation and signal processing. The signal generation and signal processing functions may occur within a common housing with the electrodes, or these functions may be packaged separately. The electrode unit electrode geometries allowed here include those described in the former patent. The disclosure of the former patent, U.S. Pat. No. 4,972,154, is included here in its entirety by reference.

Referring now to an electrode unit of the dielectric sensor, in addition to the electrode geometries described in the former patent, a new family of electrode geometries is disclosed. For each geometry of the former patent, a new geometry is defined having, in addition to the former patent geometry's electrodes, a set of symmetrical electrodes. If the original electrodes are considered to be in a front-face (operative surface) of the electrode array, the new electrodes are in a rear-face of the electrode array, and a plane of symmetry is located midway between the front and rear-faces. For each front-face drive electrode, a symmetrical rear-face drive electrode is driven with a time-varying electric potential signal equal to the negative of the signal applied to the front-face drive electrode. For each front-face seine electrode, a symmetrical rear-face sense electrode is electrically connected to it. A front-face sense electrode and its symmetrical rear-face sense electrode can be replaced by a single sense electrode provided it is located symmetrically about the plane of symmetry.

This arrangement cancels contribution to sense electrode signals from front-face drive electrodes caused by capacitive coupling through the dielectric material supporting them. Cancellation of the effect of this background capacitance $C_b$ is accomplished by an equal magnitude but oppositely signed contribution from the drive electrodes on the rear face of the dielectric supporting material. This is a different approach than for the former patent and has advantages which are made clear by this disclosure.

Art electrode unit of the present disclosure allows use of a new set of drive signals which cycle through a basic set of three time intervals instead of the two used with the former patent technology. Further definition of the drive signals allows probing at different frequencies either sequentially or simultaneously.

It will be seen that the new drive signals together with rear-face electrodes give the dielectric sensor certain advantages in determining the isotropic component of permittivity of the measured material.

In application to sensing of wood properties, an electrode unit's operative surface is positioned adjacent and substantially parallel to a plane wood surface as described in the former patent.

The advances disclosed here include signal design and signal processing steps to obtain measures of permittivity, energy loss, anisotropies in permittivity and energy loss, and direction of maximum permittivity and energy loss. The techniques described in the former patent for obtaining grain angle are retained in the dielectric sensor. Further, general processing procedures are disclosed which, in addition to grain angle, are useful in the estimation of amount of alignment, moisture content, density, species, orientation of wood machined surface with respect to growth rings, and strength.

DETAILS OF THE DIELECTRIC SENSOR

A new processing Step computes from the signals S1 and S2 a value SS given by:

$$SS = (S1^2 + S2^2)^{\frac{1}{2}}$$
$$= (k_a^2 C_v^2 \cos^2(2G) + k_a^2 C_v^2 \sin^2(2G))^{\frac{1}{2}}$$
$$= k_a C_v$$

which is proportional to the parameter $C_v$ with proportionality factor $k_a$. SS is defined as signal strength and can be treated as a measure of the amount of alignment or the amount of anisotropy of the material permittivity. The evaluation of signal strength SS has been implemented along with grain angle G in the Model 520 Grain Angle Indicator offered for sale by Metriguard Inc. of Pullman, Wash.

The signals S1 and S2 are the same signals as were used in the former patent to obtain grain angle by the division method, and they are useful for that here also. Although grain angle measurement by the division method is substantially independent of the size of the signals S1 and S2, the quantity signal strength is directly proportional to the size of S1 and S2. Signal strength depends on both the anisotropy of the material being measured and the spacing between the operative surface of the electrode unit and the surface of the material. For a material such as wood, anisotropy in permittivity depends on its moisture content, density, species and temperature, as well as its amount of alignment and microscopic character.

We disclose how to obtain a third signal S3 which is proportional to $C_o$, that is, $S3 = k_i C_o$, where $C_o$ is the isotropic component of permittivity for the specimen material and $k_i$ is a proportionality factor. Then the ratio:

$$NSS = (S1^2 + S2^2)^{\frac{1}{2}}/S3$$
$$= k_a C_v/(k_i C_o)$$

is a measure of signal strength normalized by signal S3. By attributing to the proportionality factors $k_a$ and $k_i$ the variations in sizes of signals S1, S2 and S3 which are common to all three of these signals, the argument is made that $k_a = k_i = k$, where k is a common proportionality factor. Spacing between the operative surface of an electrode unit and the surface of the measured material is an example of a variable which will affect all three signals substantially equally. Given that the proportionality factors $k_i$ and $k_a$ are identical, then:

$$NSS = C_v/C_o.$$

Because NSS has the proportionality factor due to spacing removed from it, this normalized measure of signal strength is substantially independent of spacing within an operating range, and thus it can be a more practical indicator than SS of the amount of anisotropy.

We further note that the ratio $C_v/C_o$ can be written as:

$$C_v/C_o = [(C_o+C_v)-(C_o-C_v)]/[(C_o+C_v)+(C_o-C_v)]$$

which is the, difference divided by the sum of the capacitances measured in the directions of maximum and minimum capacitance. Thus, on an intuitive basis, NSS is a good normalized measure of the amount of anisotropy.

The addition of a third time interval to the drive signals wherein all the front-face drive electrodes are driven with the same time-varying electric potential signal makes it possible to obtain a measure, S3, of the isotropic component of permittivity. Drive signals in the third time interval are basically different from those in the first two time intervals wherein, as described in the former patent, the signals are defined to cancel the effects in the measurement of the isotropic component of permittivity.

The signal S3 is proportional to isotropic capacitance comprised of the sum $C_o+C_b$ of both the desired component $C_o$ from the wood and an undesired background component $C_b$ from the dielectric supporting material for the electrodes. We disclose that by introducing another set of electrodes to the opposite side (rear-face) of the dielectric supporting material such that each of the rear-face electrodes is symmetrical with a corresponding front-face electrode, the effect of $C_b$ can be cancelled. The rear-face electrodes consist of one electrode for each of the original (front-face) electrodes and are arranged so that the entire array is symmetrical about a plane of symmetry midway in the dielectric supporting material between the front-face and rear-face electrodes. The corresponding symmetrical front-face and rear-face sense electrodes are connected together in pairs.

Each rear-face drive electrode is driven during all measurement time intervals with a time-varying electric potential signal which is instantaneously equal in magnitude but opposite in polarity to the signal applied to its corresponding front-face drive electrode. Cancellation of the effect of background capacitance occurs by this arrangement because the sense electrodes (front and rear-face) are coupled equally through background capacitances to drive electrodes having opposite polarities. By this means, the effect of $C_b$ on the sensed signal is nulled, leaving just the desired result which is proportional to $C_o$. The measurement during the first two time intervals remains proportional to the anisotropic component of capacitance, even with the rear-face electrodes in place and driven as described.

The above discussion discloses the approach used in an electrode unit to cancel the effects of coupling between drive and sense electrodes caused by dielectric material which is not part of the specimen being measured. This material which in this disclosure is defined as "background dielectric" can be the material such as the dielectric material supporting the electrodes of an electrode unit or it can be other dielectric material in the space near enough to the electrodes that it affects coupling between drive and sense electrodes. Similarly, "background conductor" is defined as conductive material other than the electrodes which is close enough to the electrodes so as to affect coupling between drive and sense electrodes. Together background dielectric and background conductor are referred to as "background material". Any coupling of the electric field either by electric displacement or conduction which acts to cause a signal at sense electrodes not due to coupling through the specimen material is defined as "background effect".

With these definitions, it will be seen that electrode units having symmetrical rear-face electrodes and drive signals to them which are equal in magnitude and opposite in polarity cause background effect to be zero if background material is symmetrical about the plane of symmetry for the front and rear-face electrodes. Usually, electrode units will be constructed so that background material is substantially symmetrical. However, all that is necessary to achieve a successful electrode unit according to the teachings of this disclosure is to cause the background effect to be zero. Thus, while conceptually easier to comprehend the symmetrical arrangement, and only symmetrical arrangements will be discussed from here on, it is to be understood that adjustments can be made in the sizes, locations and number of rear-face electrodes as well as the magnitudes and phases of drive signals going to rear-face electrodes so as to compensate for asymmetries in the background material. The basic teachings of this disclosure are to be understood as applying time-varying electric potential signals to rear-face electrodes so as to cause the background effect to be zero.

With time-varying electric potential signals applied to both front and rear-face electrodes so as to cause background effect to be zero, Signals measured at the sense electrodes are zero for all three time intervals of drive signals if no specimen dielectric material, e.g. wood, is near the electrode unit. When wood is placed near the electrode unit, the detected result for the first time interval is $S1 = kC_r\cos(2G)$, the detected result for the second time interval is $S2 = kC_r\sin(2G)$, and the detected result for the third time interval is $kC_o$. The signals S1, S2 and S3 all vary as a function of parameters such as density, temperature, species, growth ring orientation, moisture content, and distance between electrode unit and specimen. For accuracy, only negligible change can occur in these parameters during each period when a set of measurements S1, S2 and S3, is taken.

The foregoing assumes that coupling through a wood specimen is capacitive; however, it is known that as wood increases in moisture content, its conductivity, i.e. its lossy current component, increases. Thus the wood can have both a capacitive and a conductive component. Here, the capacitive component is considered to be a measure of the real part of the permittivity or dielectric constant, and the conductive component is considered to be a measure of the imaginary part of the permittivity or dielectric constant.

In the dielectric sensor, the imaginary pan of permittivity will show up as a signal at the sense plate shifted in phase when compared with the signal due to the real pan of permittivity. A capability with the dielectric sensor of the present invention results from detecting both a capacitive and a conductive component of the sensed signal. One method for doing this is to divide each signal interval into two subintervals. During each first subinterval, detection occurs as before, and a measure of the real part of the permittivity is obtained. During each second subinterval, the reference Signal used for signal detection is shifted by a quarter period of the drive signals, and a measure of the imaginary component of permittivity is obtained.

It is recognized that the real and imaginary components of material permittivity can change with frequency. There can be advantages in designing the probing signals specifically for the type of material being measured. For example, in wood it is known that the permittivity and hence capacitance is significantly greater at some frequencies than at others. To learn about moisture content, it will be desirable to probe with electric fields that can emphasize these differences. Thus, as still another advantage of the dielectric sensor, probing is allowed to occur at more than one frequency. Different probing frequencies can be implemented in more than one way. Examples illustrate how this can be accomplished.

In a first example of probing at more than one frequency, one can probe first at a first frequency, going through all three intervals and obtaining, for the first probing frequency, the signals described. Then, switch to a second probing frequency, and repeat the process. The frequency of the reference signal used during detection is adjusted to correspond with the probing frequency. This sequence at different probing frequencies can be repeated for as many probing frequencies as desired or as practical. It will usually be desirable to adjust the time period during which all the probing frequencies are used so that it is short enough to be completed before anything else changes significantly in the measurement. For the situation where material is moving past the electrode unit, this condition is similar to the concept of "stopping motion" with fast shutter speeds when taking photographs of moving objects.

In a second example of probing at different frequencies, the drive signals are composites of different frequency components, where the different frequency components are orthogonal to each other over a measurement period. In this case, detection at the different frequencies occurs simultaneously. A parallel detection arrangement is used, where a plurality of reference signals (demodulating signals) are each matched for a particular frequency component. In the case where measures of both real and imaginary parts of permittivity are to be detected, either two detectors (one for each of the real and imaginary parts) can be used for each frequency component, or the measures of real and imaginary parts can be detected sequentially by alternately changing the reference signal of just one detector for each frequency.

There are signal processing and detection advantages in using a set of orthogonal reference signals and an array of detectors, one detector for each reference signal. It will be clear to those skilled in the art that the first example of probing at different frequencies can be put also into the orthogonal reference signal framework because the different frequencies occur during mutually exclusive time intervals; hence the reference signal defined there could be redefined as a sum of orthogonal components, with nonzero values during mutually exclusive time periods. Although the discussion is introduced here with the use of different frequency components that are orthogonal, it will be clear that any set of orthogonal signals can be used in this approach.

The description of the preferred embodiment of this disclosure contains more details of detection. A good reference is *Principles of Communication Engineering* by J. M. Wozencraft and I.M. Jacobs, John Wiley & Sons, New York, NY, 1965. Matched filtering techniques can also be used to implement detection. Details of matched filtering techniques are described by Wozencraft and Jacobs.

Auxiliary variables that can be considered in the dielectric sensor include: spacing between electrode unit and material to be measured, type of material to be measured if it is not always the same (e.g. different species in wood), material temperature, density, moisture content, contamination of the electrode unit operative surface and the lack of parallel alignment of the electrode unit's operative surface with respect to the surface of the measured material.

Some of these auxiliary variables are best dealt with by controlling their amounts so they don't significantly influence the result. Other auxiliary variables can be measured by independent means and their effects on the measurement compensated. But, it may be desirable to estimate values of some variables as part of the measurement process. The probing signals used by the dielectric sensor can be designed or selected to enhance estimation for the particular variables desired.

In general, three types of variables are defined here: auxiliary variables (controlled or measured by independent means), variables measured by the dielectric sensor and variables estimated by the dielectric sensor. The application determines which one of these categories a variable is in. For example, the moisture content of wood may be known as a result of its conditioning for a period of time at known relative humidity and temperature or it can be measured by independent means. In this case, moisture content is an auxiliary variable and can be used as input to the dielectric sensor for use in the estimation of other variables. Or, the dielectric sensor itself, by measurements of dielectric properties, can provide an estimate of moisture content. To do this, the dielectric sensor may use auxilary variables, for example, temperature, in the estimation process.

The output of the dielectric sensor may consist of estimates for particular variables as discussed. Another step can be taken in which the values for the variables including auxiliary, measured and estimated variables are used as inputs to a classification step. As an example, the output of the classification step applied to these values for lumber can be a lumber grade which identifies how the lumber can be used.

The dielectric sensor can use both auxiliary variables and variables measured by the dielectric sensor as inputs in an estimation process. The preferred embodiment of this disclosure discusses use of multiple linear regression for estimation. Other estimation techniques can be used also.

In general, when faced with highly complex data (many dimensions in a vector representation), pattern recognition methods can be used. Here, pattern recognition is viewed as data processing in which first the data complexity may be reduced by feature extraction and then a classification step identifies the data as belonging to one of several categories. Depending on the application one or the other of these steps may be bypassed. Multiple linear regression is treated here as an example of feature extraction where several dimensions are reduced to a single dimension. Standard methods can be used for a classification step. Numerous articles have been written on this subject. A survey article by Fu, King-Sun, "Recent Developments in Pattern Recognition," IEEE Transactions on Computers, Vol. C-29, No. 10, Oct. 1980, provides an introduction to pattern recognition with an extensive list of references.

Here, a pattern is considered to be a vector whose components are the auxiliary and measured variable values. During a training period, patterns having known classification, called "training patterns", are each located in a multi-dimensional vector space called pattern space. This is done by measurement with the dielectric sensor. Thus each training pattern becomes a vector in pattern space. The number of dimensions of the pattern space is the number of variables. Using the training patterns, a classification process identifies regions of the pattern space that are more likely to be from one class than from another, and then it classifies these regions according to their most likely class. A pattern with unknown class is classified according to the class of the pattern space region in which it falls.

If the dimensionality of the pattern space is too large to be practical, a "feature extraction" step may be desirable. Feature extraction maps or transforms the pattern space into a feature space. The number of component features comprising the feature space, i.e. the dimensionality of the feature space, is typically much less than the number of component variables defining the pattern space. A goal of the feature extraction step is to reduce dimensionality (complexity) of the data and yet retain the separability of the classes for patterns represented in the feature space. It is to be understood that this description is only a review of pattern recognition ideas which are thoroughly covered in the literature. Processing of data in the dielectric sensor can include any of the known methods of pattern recognition.

For an example of the pattern recognition process as it can be applied with the dielectric sensor, suppose each piece in a sample of lumber is measured by the dielectric sensor together with apparatus for obtaining any auxiliary variables required. Let classification be defined as tensile strength being either above or below 10,000 psi [70 MPa]. Then, each of these pieces of lumber becomes a training pattern in a pattern space if it is tested to failure in tension and classified according to its strength. The components of the pattern space are the variables measured by the dielectric sensor and the auxiliary variables. By whatever means, e.g. by methods described in the text *Decision-Making Processes in Pattern Recognition* by G.S. Sebestyen, The Macmillan Company, New York, NY, 1962, the training patterns can be used to classify the pattern space.

As an example of feature extraction, the pattern space can be transformed to a one-dimensional feature space whose single dimension is estimated tensile strength. One method for doing this is to perform a multiple linear regression of measured strength on all the components of the pattern space. The feature space is then classified with a threshold at 10,000 psi [70 MPa]. A piece of lumber can be classified according to strength by obtaining its pattern with measurements from the dielectric sensor and auxiliary apparatus, transforming the pattern to the feature space and comparing the transformed pattern with the threshold.

To summarize, the dielectric sensor offers the capability of efficiently measuring dielectric properties of a dielectric material specimen, compensating or including the effects of auxiliary variables, extracting features important in the use of the dielectric specimen and classification of the specimen into one of several categories.

It is to be understood that data from either one or more than one location on the measured material may be used in the process. The following is an example where data from more than one location is gathered for use in estimating a property of interest.

Grain angle obtained from the dielectric sensor at multiple points over the surface of flakeboard can be used to estimate the amount of alignment of the flakes in the flakeboard. This processing approach uses definitions of directional data contained in the text *Statistics Of Directional Data* by K.V. Maralia, Academic Press, 1972. We disclose how to make the dielectric sensor function as a processor of directional data. The dielectric sensor can estimate amount of alignment either from multiple measurements of grain angle at a number of representative points on the flakeboard surface or from a measurement of the anisotropic component of permittivity at a single point on the flakeboard surface. More details are included in the description of the preferred embodiment. These methods for estimating the amount of alignment in flakeboard are understood to be applicable to other dielectric materials whose constituent particles have a distribution of alignment directions.

As will be seen, the concepts described for flakeboard can be used to obtain information about the flake size distribution.

BRIEF DESCRIPTION OF THE DRAWINGS

The preferred embodiment of the invention is illustrated in the accompanying drawings, in which.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

Figure 1:
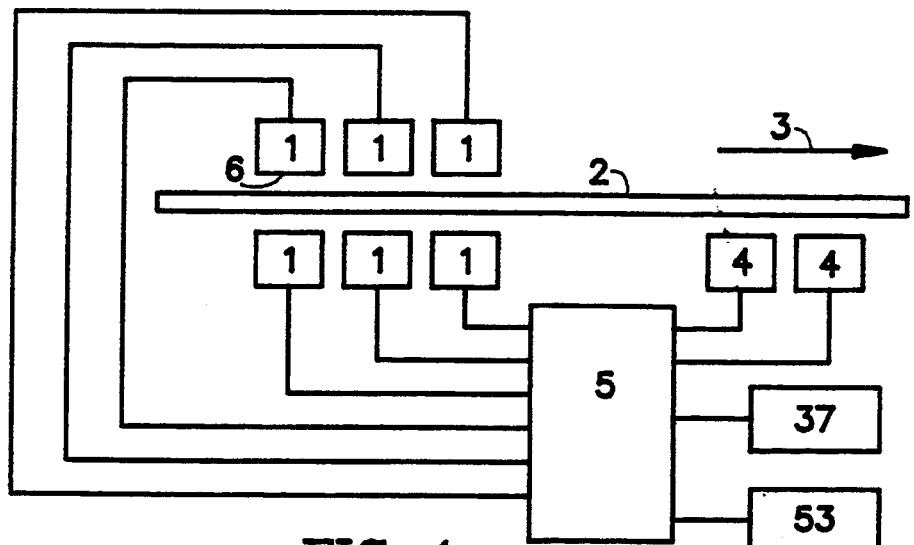
FIG. 1 is a schematic elevation view of the dielectric sensor in a testing environment.
Figure 2:
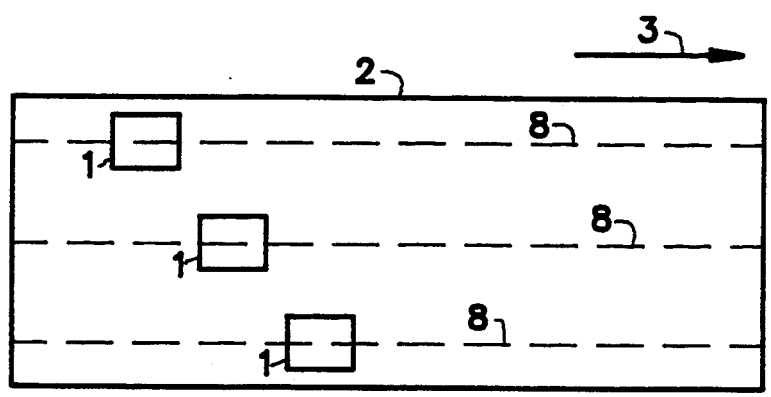
FIG. 2 is a schematic plan view of three dielectric sensor electrode units arranged so as to sense dielectric property information along three tracks on the surface of a dielectric panel.

FIG. 1 and FIG. 2 illustrate the environment in which the dielectric sensor is used. In FIG. 1, an elevation view shows an example where six electrode units 1 are arranged about the surface of a dielectric material specimen 2 moving in direction of arrow 3. The specimen could be a wood board, a wood composite panel, or other dielectric material. In FIG. 2, a plan view shows the three electrode units 1 of FIG. 1 which are above the dielectric specimen arranged so as to obtain information from the specimen along three longitudinal tracks defined by motion of the specimen relative to the electrode units. In FIG. 2, the specimen 2 is illustrated as though it were a wood panel, for example flakeboard.

Also shown in FIG. 1 is optional auxiliary sensing apparatus 4. The purpose of the auxiliary sensing apparatus is to provide auxiliary measurements using known technology such as infrared radiometers for temperature, gamma gauges for measuring density and follower wheels and arms or other methods for measuring distances between wood and electrode units. In some cases these auxiliary variables may be known or controlled as part of the apparatus. In this embodiment, some variables estimated by the dielectric sensor for one example may be known or measured by auxiliary sensor apparatus in another example. Auxiliary variable data from auxiliary sensors become input for processing along with data from the electrode units.

FIG. 1 illustrates electrode units 1 near upper and lower surfaces of dielectric specimen 2; however, these electrode units can be positioned as desired about the specimen's surface, including both faces and both edges in the case of a specimen having rectangular cross-section. The operative surface 6 of each electrode unit 1 must be positioned substantially parallel and adjacent to a flat part of the specimen's surface. Timing, control, signal generation and processing are accomplished in control and processing unit 5 which accepts inputs from electrode units 1 and from auxiliary apparatus 4. From control and processing unit 5, instructions are sent for control of output apparatus 53. Output apparatus can include monitors, marking equipment, sorting equipment, and/or drying and sawing devices. For example, a trim saw can be controlled to remove local characteristics in the wood which are sensed as having excessive grain angle or as having insufficient anisotropy.

Figure 3:
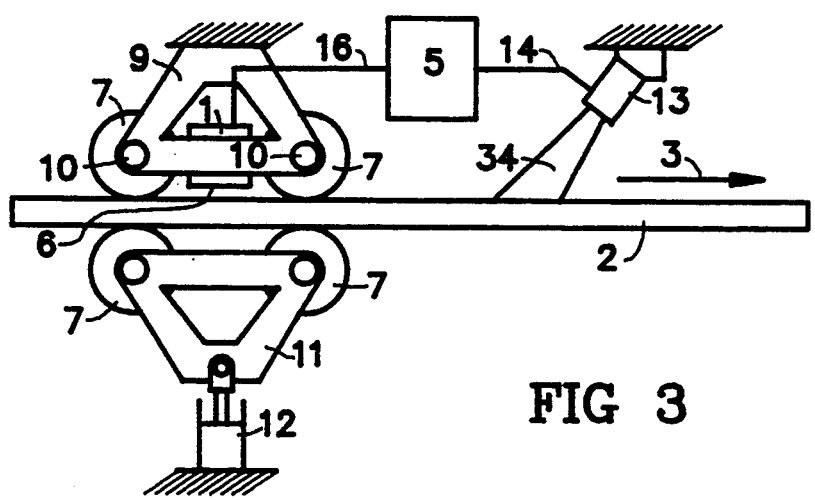
FIG. 3 is a schematic elevation view of one electrode unit of a dielectric sensor and an auxiliary temperature measuring input device, the electrode unit being held in a controlled position relative to the surface of the tested material.

To show the generality of the preferred embodiment, consider using the dielectric sensor for estimating moisture content in a wood board specimen. Let spacing between a flat surface of the board and an electrode unit of the dielectric sensor be a controlled auxiliary variable. Spacing is controlled with clamp rollers 7 above and below the wood board 2 as shown in FIG. 3 where an electrode unit 1 is mounted on a clamp roller carriage 9 supporting the rollers 7 at beating points 10. Rollers of similar clamp roller carriage 11 squeeze the wood board against rollers of clamp roller carriage 9 by means of air pressure applied to air actuator 12. This arrangement fixes the vertical position of the wood board and also the spacing of the electrode unit operative surface 6 relative to a flat surface of the wood board. This example illustrates only one electrode unit, but it is clear that more than one electrode unit can be positioned near any flat surface of the wood board, including both upper and lower faces and both edges of the board. In the present example, the lateral position of the wood board specimen is controlled by lateral air-spring loaded fixed guides (not illustrated).

The clamp rollers can also be used to provide motive force so as to cause the wood board to roll through the apparatus by means of motors (not shown) coupled to one or more of the rollers. Clamp roller systems similar to this are common in other equipment, for example, the CLT Continuous Lumber Tester manufactured by Metriguard Inc. in Pullman, Wash. and Irvington Moore in Portland, Oreg.

In this example an auxiliary variable, temperature, is provided. A number of instruments for this are available one of which is the Model ET3LT radiometer by Raytek Corp of Santa Cruz Calif. The radiometer antenna 13 with antenna pattern 34 is aimed at the surface of the board so the temperature of a defined area of the board can be read and processed to give a signal on cable 14 suitable for use by the dielectric sensor control and processing unit 5. Alternatively, the temperature can be input as a known variable if the lumber has been controlled to a known temperature.

Information about the specimen's dielectric properties is sent via cable 16 to the control and processing unit 5. There, measures of isotropic and anisotropic components of permittivity, $C_o$ and $C_v$, are obtained at two frequencies by methods to be described. Because a region of the specimen sensed by the dielectric sensor electrode unit is not sensed simultaneously by the radiometer, knowledge of distance between the sensed areas as well as the speed of the board is required by the control and processing unit. This information can be read into the processor through other auxiliary apparatus (not shown in FIG. 3) or by operator interface. The control and processing unit 5 uses well-known signal delay and processing techniques to identify temperature data and data from the dielectric sensor electrode unit with specific sensed regions of the specimen.

In this example, estimated moisture content is the end result, and a classification step is unnecessary. However, the process including classification is described to complete the example. First, patterns are defined as vectors in a five-dimensional pattern space where the dimensions are temperature, $C_o$ at two frequencies and $C_v$ at two frequencies.

Training patterns are obtained by taking temperature and dielectric measurements at a number of locations in wood specimens where the moisture content has been carefully determined by other means, for example, by methods described in ASTM Standard D2395 available from the American Society of Testing and Materials in Philadelphia, PA. Multiple linear regression of moisture content on the five variables of the pattern space gives an estimating function for moisture content in terms of the five pattern variables. This mapping or function which reduces the five-dimensional pattern space to a one-dimensional feature space is an example of feature extraction.

Sometimes it is advantageous to form new variables which are functions of the original variables. The dimensionality of the pattern space may thereby increase if all original variables are retained as well as the new ones.

Figure 4:
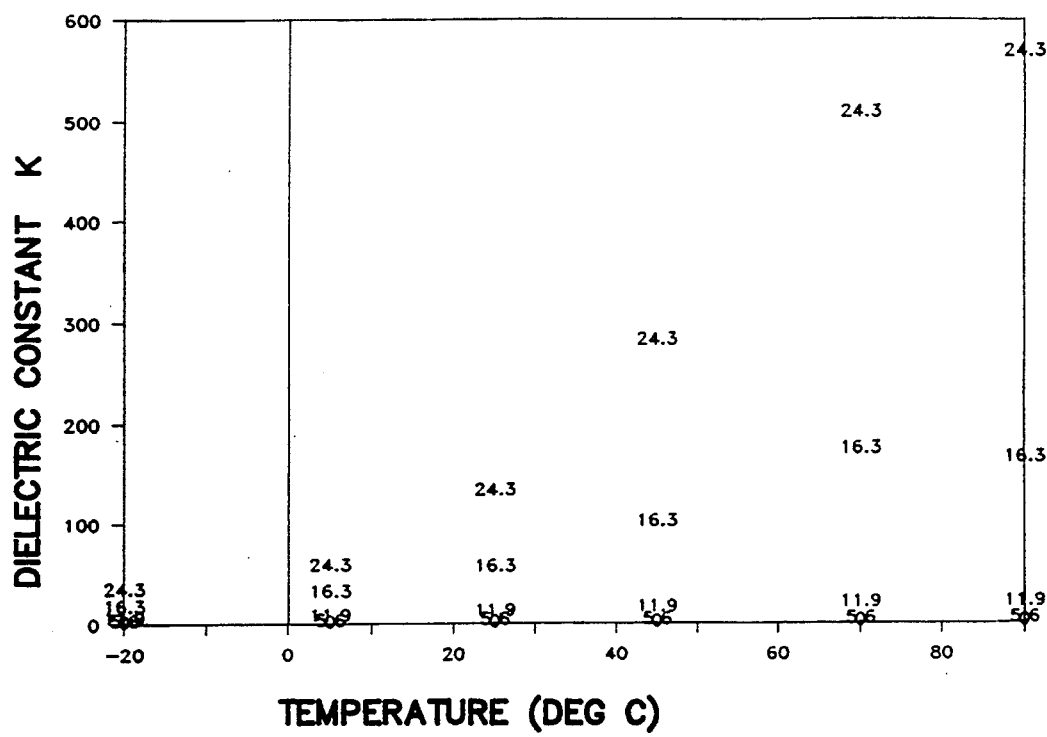
FIG. 4 illustrates dielectric constant versus temperature for a specimen of lumber at five different moisture contents, the data adapted from James 1975.
Figure 5:
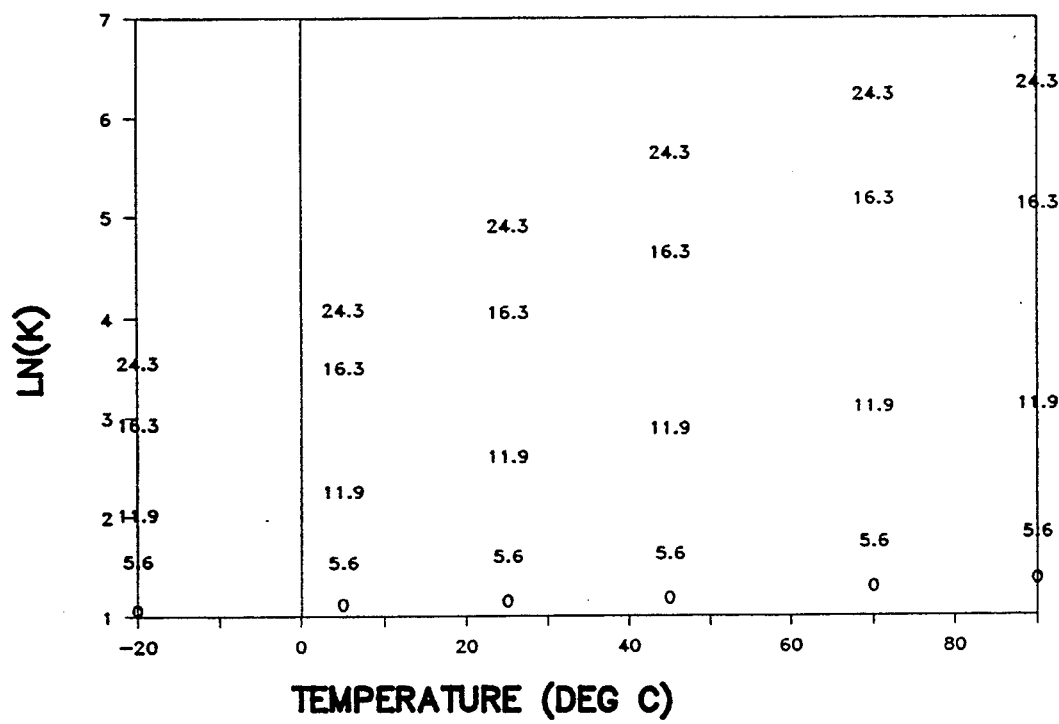
FIG. 5 illustrates the same data as in FIG. 4 but with the ordinate transformed by the natural logarithm function so that the different moisture contents are more geometrically separated in this transformed space.

To show these concepts specifically and pictorally as used with the dielectric sensor for the estimation of moisture content, a pattern space of two-dimensions is illustrated in FIG. 4. In FIG. 4, the abscissa variable is temperature T, and the ordinate variable K is a measure of isotropic capacitance $C_o$ at one frequency. The numbers for points plotted in the pattern space are moisture contents for training patterns located at those points in the pattern space. This data, adapted from James 1975, is for Douglas fir (Pseudotsuga menziesii). A study of the training pattern locations in the pattern space of FIG. 4 suggests that the separability of patterns having different moisture contents can be enhanced by a transformation of the pattern space. Instead of the variable K, the pattern space is modified to use LN(K) as illustrated in FIG. 5, where LN denotes the natural logarithm function. As can be seen by comparing the pattern spaces of FIG. 4 and FIG. 5, this nonlinear transformation has had the effect of separating for better visualization the regions of different moisture content. Further, FIG. 5 suggests the function $LN(K)=a+bM+cMT$ as a reasonable fitting function, where a, b and c, are fitting parameters, M is moisture content and T is temperature. Multiple linear regression of LN(K) on the two variables M and MT yields the parameters a, b, and c. Although the fitting is to an inverse relationship, the resulting equation can be solved for estimated moisture content as a function of K and T. We label this estimated moisture content $M_e$ and write $M_e=(LN(K)-a)/(b+cT)$. This is an example of extracting the one-dimensional variable $M_e$ from the two variables T and K.

Figure 6:
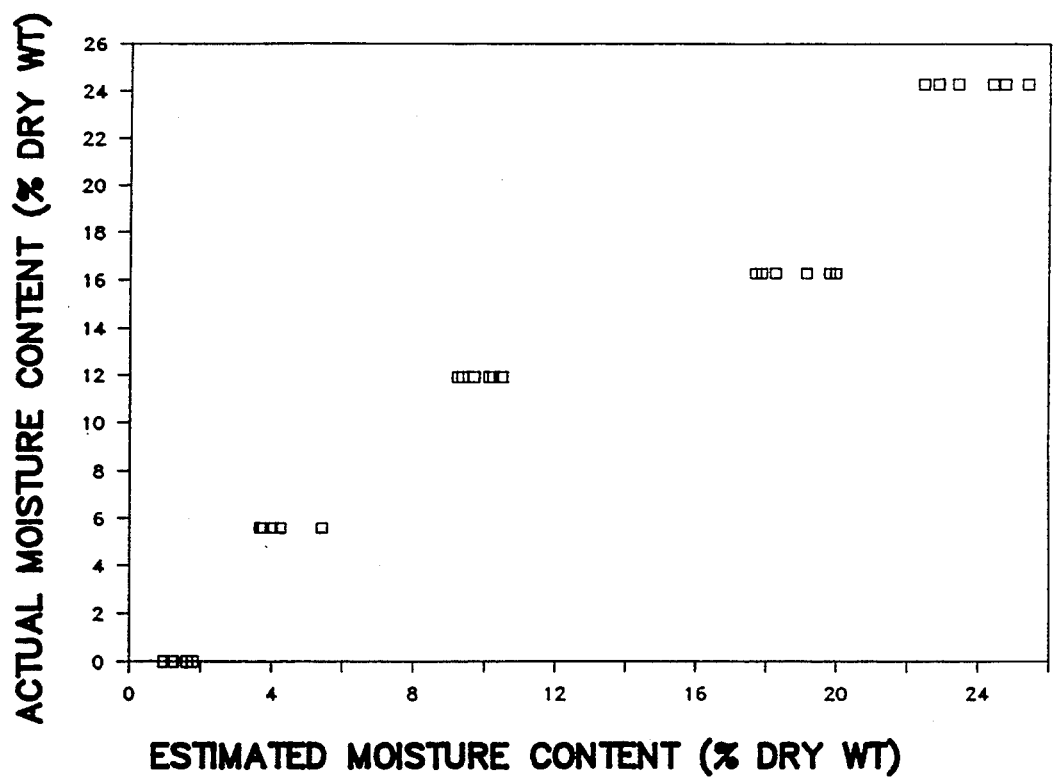
FIG. 6 illustrates, for the data represented in FIG. 4 and FIG. 5, moisture content versus estimated moisture content, the estimated moisture content being determined as a function of temperature and dielectric constant.

If classification into moisture content categories is desired, this can be accomplished either with thresholds in the single variable $M_e$ feature space or with corresponding lines of constant $M_e$ in the pattern space as defined by the equation $LN(K)=a+bM_e+cM_eT$ in FIG. 5, or $K=\exp(a+bM_e+cM_eT)$ in the original pattern space of FIG. 4. FIG. 6 illustrates moisture content M plotted against estimated moisture content $M_e$ for this example of the use of the preferred embodiment.

This example has illustrated use of the dielectric sensor and auxiliary measurements in the definition of a pattern space, transformation of the pattern space, an inverse function procedure in determining a fitting function and estimation of a desired quantity. Classification has also been discussed. The intent is to show by visualizable example the generality and capability of the dielectric sensor. It is clear that it is not necessary to restrict the pattern space to five dimensions or limit processing to just two dimensions as in the example.

FIG. 1 and FIG. 2 show a plurality of electrode units for the dielectric sensor, with the electrode units arranged about the surface of the dielectric material specimen. Electrode units in an array must be spaced far enough apart from each other that measurements by any particular unit are not affected by the presence of another electrode unit. In some cases it has been found that electrode units can be positioned more closely if their signals are time-multiplexed so that only one is active at a time. For example, time-multiplexed electrode units have been found to operate successfully in the same plane at a center-to-center spacing of 3 inch [76 mm]. By well-known signal-delay methods, measurements from several detectors can be organized into patterns representative of more closely or more distantly spaced regions on the specimen than the electrode unit spacings.

Figure 7:
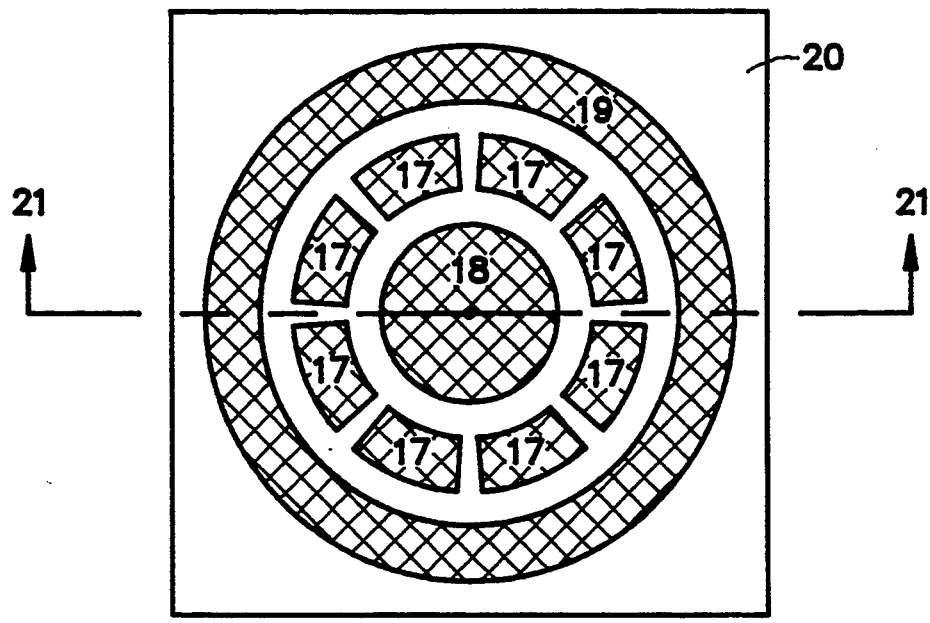
FIG. 7 is a simplified front-face view of an electrode unit electrode array.

FIG. 7 is a simplified front-face view of an electrode unit of the preferred embodiment. Drive electrodes 17, sense electrode 18, and shield electrode 19 are arranged about an electrode unit axis in the center of the electrode array, the electrode unit axis being substantially perpendicular to the operative surface of the electrode unit. Here, the operative surface of the electrode unit is the plane which best fits the front surfaces of the front-face electrodes which are shown hatched in FIG. 7. Constraints of the different geometries allowed for the front-face electrodes are the same as those for the electrodes disclosed in the former patent (U.S. Pat. No. 4,972,154). The former patent used only front-face electrodes.

Figure 8:
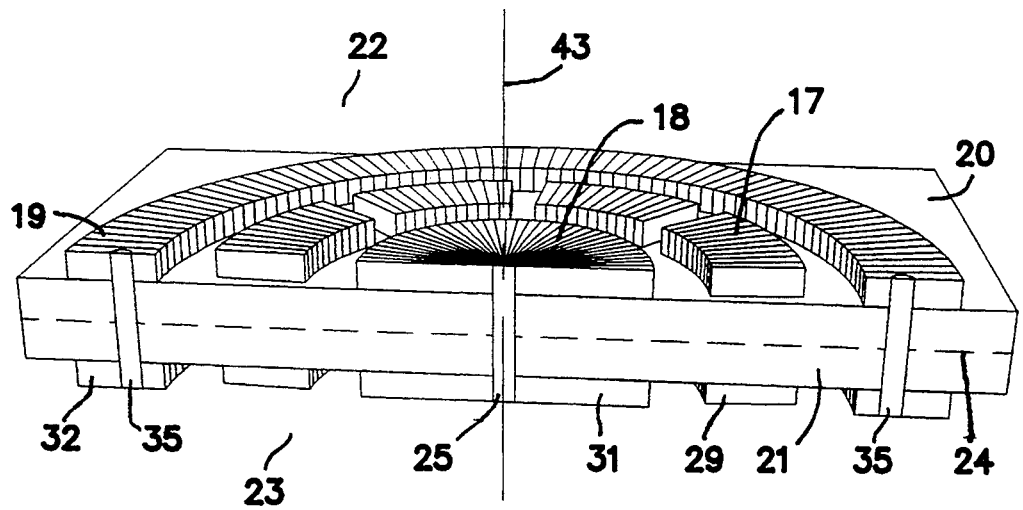
FIG. 8 is a cutaway perspective edge view of the electrode unit electrodes in FIG. 7 as it would look if cut along the diametral cutting plane shown in FIG. 7 and illustrates rear-face electrodes which are arranged symmetrically with the front-face electrodes.

The arrangement of FIG. 7 is implemented as a printed circuit board where the electrodes are formed of metal bonded to a composite substrate of fiberglass and resin 20. Rear-face electrodes are positioned on the back surface of this double-sided printed-circuit board so that the front-face and rear-face electrodes form a symmetrical sandwich with the fiberglass substrate. The plane of symmetry is in the fiberglass substrate parallel to the front and rear-faces and midway between them. FIG. 8 is a cutaway perspective edge view of the electrode unit of FIG. 7 along cutting plane 21. The thicknesses of the front-face 22 and rear-face 23 electrodes are exaggerated for clarity. The plane of symmetry between front-face and rear-face electrodes is midway between them and lies in the fiberglass substrate; the edge of this plane of symmetry where it intersects the surface of cutting plane 21 is illustrated as dotted line 24 in FIG. 8. Front-face sense electrode 18 and rear-face sense electrode 31 form a symmetrical pair and are connected together with plated-through hole 25 which also serves as a connection point for the sense electrode pair. Similarly, the front-face shield electrode 19 and rear-face shield electrode 32 are connected together as a symmetrical pair by plated through holes 35. Each front-face drive electrode 17 and symmetric rear-face drive electrode 29 are connected to sources of time-varying electrical potential signals that are equal in magnitude but opposite in polarity as illustrated schematically in FIG. 9. Time-varying electric potentials V1 and V2 are denoted separately in FIG. 9, although for the preferred embodiment, drive electrodes located diametrically opposite one another as shown in FIG. 9 would have the same applied voltage.

Figure 10:
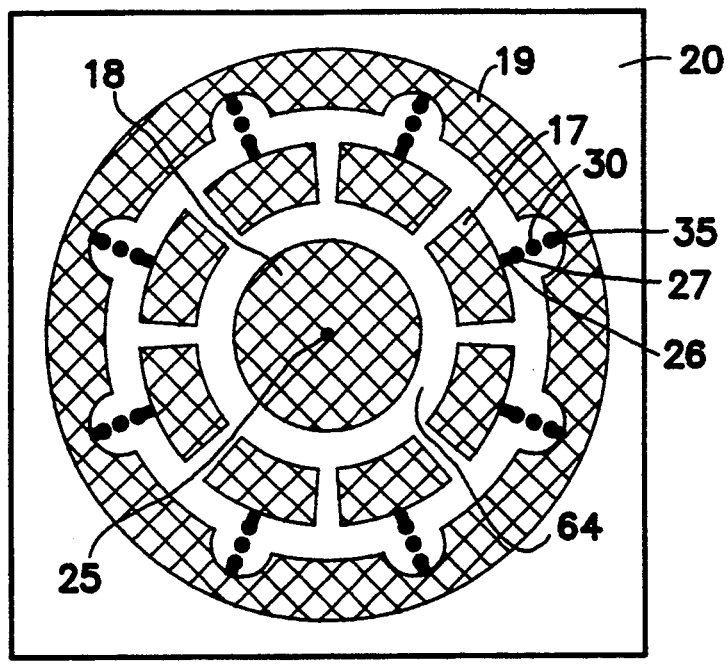
FIG. 10 is a detailed front-face view of an electrode unit electrode array illustrating means of connecting to drive, sense and shield electrodes.
Figure 11:
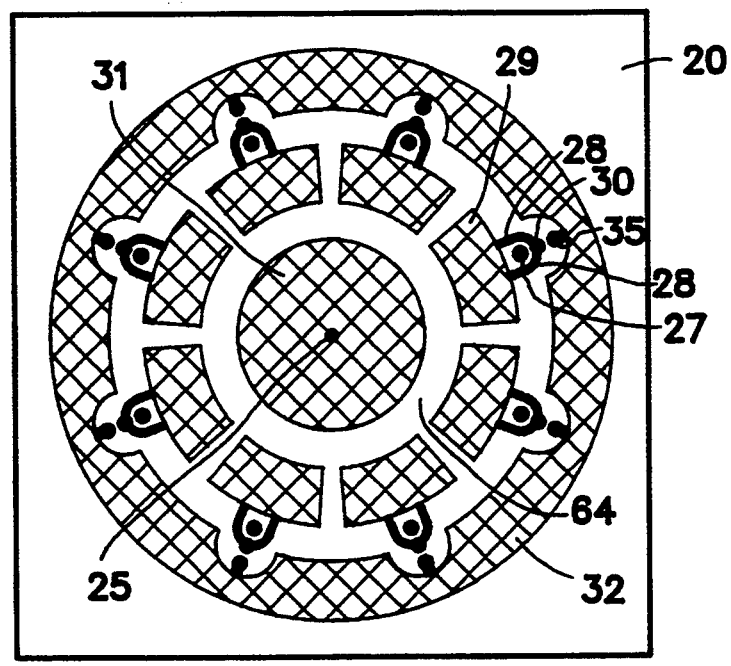
FIG. 11 is a detailed rear-face view of an electrode unit electrode array illustrating means of connecting to drive, sense and shield electrodes which are symmetrically positioned with respect to the front-face electrodes.

FIG. 10 and FIG. 11 illustrate respectively additional details of the front-face and rear-face electrodes for the electrode unit printed circuit board. Printed circuit traces 26 connect front-face drive electrodes 17 to plated-through holes 27 which serve as connection points for application of electric potential signals. Similarly, printed circuit traces 28 connect rear-face drive electrodes 29 to plated-through holes 30. The connecting traces 26 and 28 are designed and located far enough away from the region 64 between drive electrodes 17 and 29 and sense electrodes 18 and 31 so that the front versus rear-face asymmetry of these traces does not affect the essence of the symmetrical relationship between front and rear-face electrodes for measuring electrical properties. Note, however, that for each pair of symmetric front-face and rear-face drive electrodes, their connecting traces 26 and 28 have a symmetry about a plane defined by the electrode unit's axis 43 (reference FIG. 8) and a straight line perpendicular to the axis and going through the midpoint of an associated drive electrode.

Figure 9:
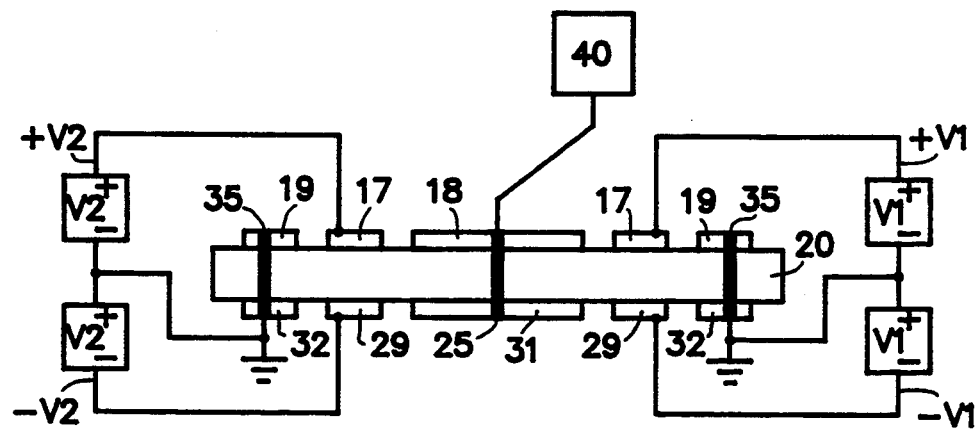
FIG. 9 is a schematic edge view showing the cross-section defined by the cutting plane of FIG. 7 and illustrating equal magnitude but oppositely signed voltages applied to symmetrical pairs of drive electrodes.
Figure 12:
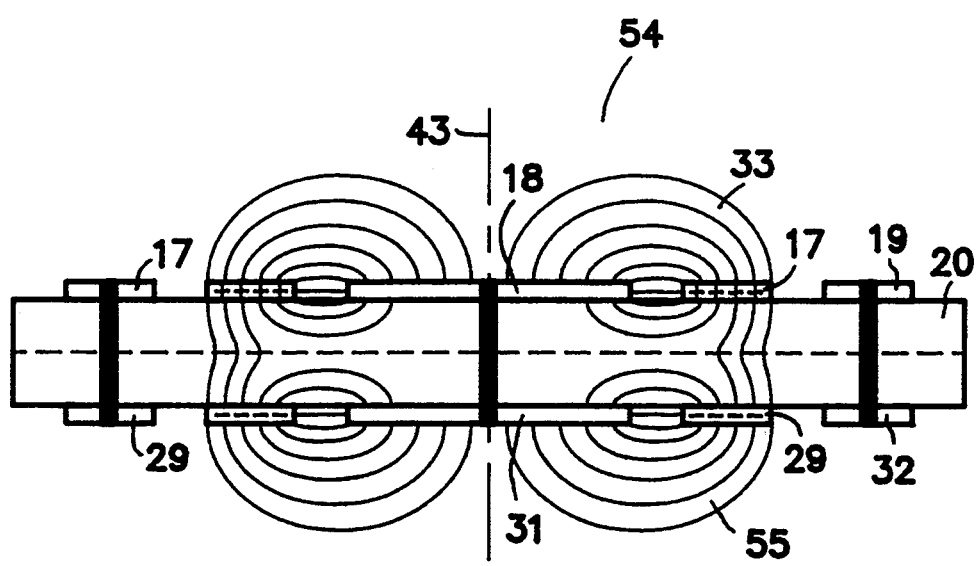
FIG. 12 is an edge view of the electrodes and dielectric substrate similar to FIG. 9 and illustrates cancellation of the effects of the electric flux field which fringes about the drive and sense electrodes through the dielectric substrate and surrounding dielectric medium.

For time-varying electric potential signals applied to symmetric front and rear-face drive electrode pairs, FIG. 12 illustrates, with a cutaway edge view similar to FIG. 9, the electric flux pattern of the electric field that fringes from the drive electrodes to the sense electrode pair. It will be seen from FIG. 12 that the signal caused at the sense electrode pair 18 and 31 by the electric field 33 due to fringing from each front-face drive electrode 17 through the dielectric substrate 20 and surrounding dielectric medium 54 is cancelled by an equal magnitude but oppositely signed signal caused by the electric field 55 from the corresponding symmetric rear-face drive electrode 29. By this method, the effect of isotropic background material, such as the fiberglass printed circuit board substrate, is substantially removed so long as each rear-face electrode is driven with a time-varying electric potential signal that is the negative of the signal applied to its symmetric front-face electrode. It is to be noted that the dielectric substrate background material, in this case fiberglass, must be substantially isotropic and symmetric with respect to a plane of symmetry in the dielectric substrate midway between the front and rear-face electrodes. Deviations from the isotropic and symmetry conditions can be compensated with deviations in definition of rear-face drive electrodes and drive signals applied to them as discussed previously.

The invention of the former patent achieved cancellation of isotropic background effects with just front-face electrodes. However, that invention was concerned with measuring an anisotropic property (grain angle), and cancellation of background effect was achieved by applying a time-varying electric potential signal to some of the front-face drive electrodes with polarity opposite of that applied to the others. The former patent explains allowable options for front-face electrodes and drive signals and deviations from the front-face electrode geometry of FIG. 7, FIG. 8 and FIG. 9 that are allowed.

In the dielectric sensor, isotropic dielectric properties of the specimen as well as anisotropic properties can be measured. The dielectric sensor is driven part of the time so as to achieve the advantages of the former patent in measuring grain angle, but part of the time it is driven to measure the specimen's isotropic properties whose effects the apparatus of the former patent cancelled. The symmetric rear-face electrodes, when properly driven as described, make practical a measure of the isotropic component of permittivity for the measured material with background effects removed. And, when the front face electrodes are driven as in the former patent, but with negative signals applied to the rear-face electrodes as disclosed here, all the advantages of the former patent technology in measuring anisotropic properties still apply.

Figure 13:
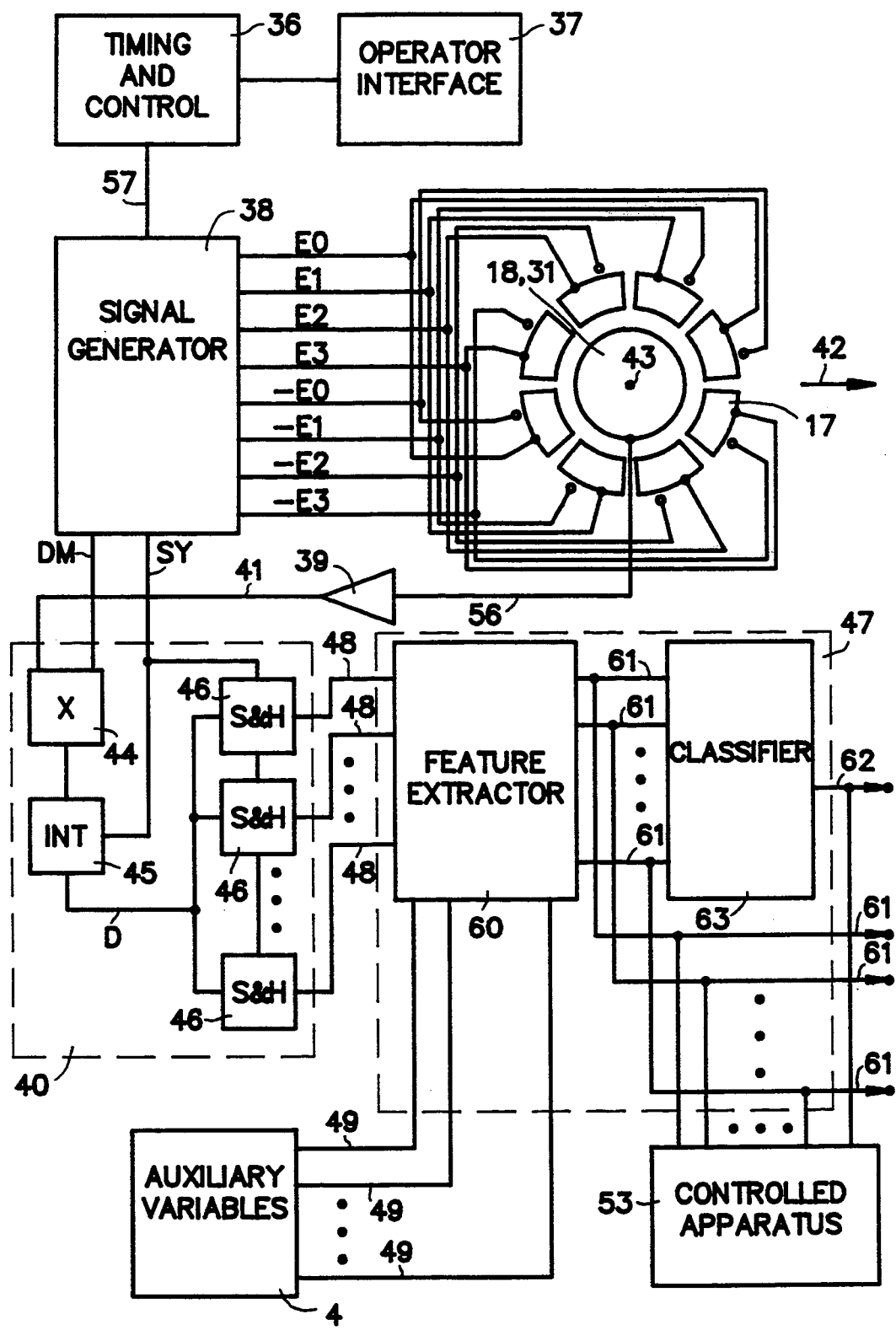
FIG. 13 is a schematic block diagram illustrating major components of the dielectric sensor and interconnections.
Figure 14:
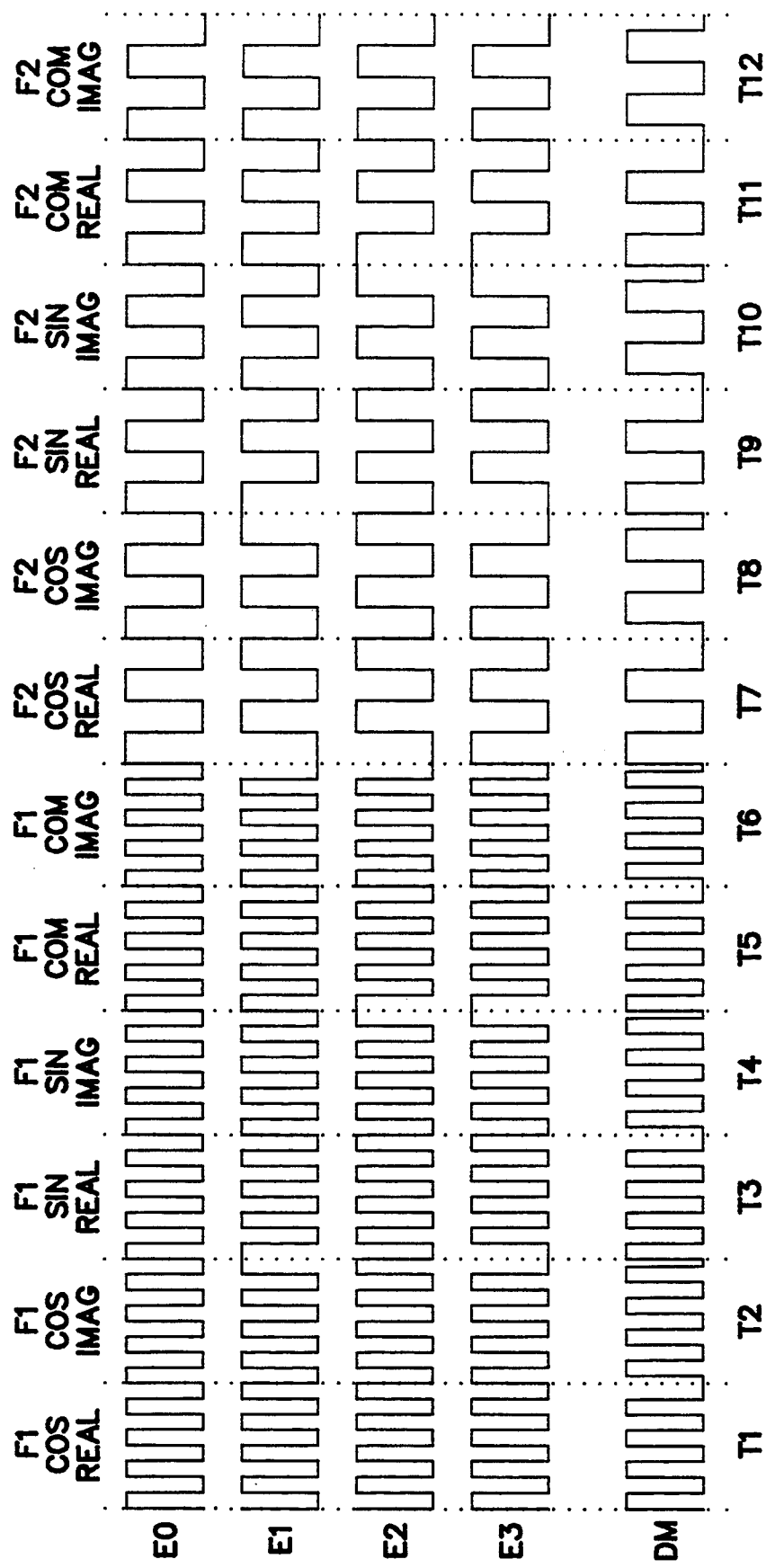
FIG. 14 illustrates drive and reference signals used in a serial implementation of powering the drive plates of the dielectric sensor and demodulating the electrode unit signal as in FIG. 13.

FIG. 13 is a schematic block diagram of the dielectric sensor illustrating timing and control, signal generation, demodulation, feature extraction and classification. The timing and control unit 36 directs the measurement sequence. The measurement sequence can be completely automatic and self-contained within the timing and control block, or it can accept inputs from and provide information to an operator by means of an operator interface 37. Signals from the timing and control unit control the signals from signal generator 38 over cable 57. Referring also to FIG. 14, time-varying electric potential signals E0, E1, E2 and E3 from the signal generator 38 of FIG. 13 are illustrated. The signals E0, E1, E2 and E3 are applied to front-face electrodes 17 of a electrode unit oriented with respect to reference direction 42 as illustrated in FIG. 13. The negatives of these signals are applied to the corresponding rear-face electrodes as shown schematically in FIG. 13 by connection dots not touching the front-face electrodes shown.

Not illustrated in FIG. 13 are the guard electrodes 19 and 32 of FIG. 8 which are connected to ground potential.

The signal 56 from the connected front-face and rear-face sense electrodes 18 and 31 is amplified by amplifier 39 to yield signal 41. Signal 41 is detected by demodulator 40 using reference signal DM and synchronization signals SY from signal generator 38. In FIG. 13 only one reference signal, multiplier and integrator combination is necessary because the combination of time-varying electric potential signals E0, E1, E2 and E3 applied to the drive electrodes and reference signal DM are defined in sequential time intervals as shown in FIG. 14 to achieve the results desired. With this configuration, time-multiplexed results appear on the detected signal D. Using the signals of FIG. 14 as described, the effect (background effect) of the isotropic dielectric supporting material (background material) for the electrodes is substantially cancelled; hence the following description of dielectric property detection refers to the material being tested and not the background material.

With reference to FIG. 14, in time intervals T1 through T6, the drive signals probing the dielectric material are square waves at frequency F1, and in intervals T7 through T12, these probing signals are square waves at frequency F2. This sequence is replicated periodically with a period equal to the sum of the time intervals T1 through T12. During each of the time intervals Ti, where Ti can be any of the time intervals T1 through T12, a particular piece of information is obtained about the dielectric material.

Demodulation of the signal during each time interval Ti occurs by multiplication of the amplified signal 41 by reference signal DM in multiplier 44 and integration of the resulting pro-duct in integrator 45 over time interval Ti. The integrated signal is sampled and held at the end of time interval Ti by the $i^{th}$ sample and hold circuit 46. At the beginning of the next time interval, integrator 45 is reset to zero, and integration is begun again. Synchronization signals in cable SY are applied to the demodulator to control the sample-and-hold and integrator-reset functions of the alemodulator. The result is a set of signals 48 at the outputs of the sample-and-hold circuits, each of which contains a piece of information about the dielectric specimen for the region being measured. Demodulation as described is an example of coherent detection which is well known to those skilled in the art.

In describing further the results from this preferred embodiment, consider use of signals as illustrated in FIG. 14 with the system illustrated in FIG. 13. In time interval T1, the detected signal D is a measure of the real part of the permittivity or capacitance parallel to the reference direction 42 relative to the amount in a direction perpendicular to both the reference direction and the electrode unit axis 43. In time interval T2, the detected signal D is a measure of the imaginary part of permittivity parallel to the reference direction relative to the amount in a direction perpendicular to both the reference direction and the electrode unit axis. This difference between results from time intervals T1 and T2 is effected by the quarter period phase shift of reference signal DM during time interval T2 compared with time interval T1 as illustrated in FIG. 14.

In time intervals T3 and T4 respectively, the detected signal D is a measure of the real part and then the imaginary part of permittivity just as in time intervals T1 and T2, except that in T3 and T4 the measures are for the direction at angle 45 degrees (or 225 degrees) from the reference direction relative to the amount at 135 degrees (or 315 degrees) from the reference direction and perpendicular to the electrode unit axis.

This difference in probing direction between intervals T1 and T2 versus intervals T3 and T4 is a result of differences in the drive signals. Careful examination of FIG. 14 will reveal that time-varying electric potential signals during intervals T1 and T2 are pairwise identical E0=E3 and E1=E2; whereas, during intervals T3 and T4 different pairs are identical, E0=E1 and E2=E3. A complete general description of drive signals required to accomplish this measurement of anisotropy is contained in the former patent.

In time intervals T5 and T6 respectively, the detected signal D is a measure of the real part and then a measure of the imaginary part of the permittivity equally weighted in all directions of a plane parallel to the operative surface of the electrode unit. The equal weighting is accomplished by driving all front-face drive electrodes with the same time-varying electric potential signal and all rear-face drive electrodes with the negative of this signal. Examination of FIG. 14 will reveal that during time intervals T5 and T6, E0=E1=E2=E3. This common time-varying electric potential signal applied to the front-face drive electrodes together with the negative of it being applied to the rear-face electrodes allows the isotropic component of capacitance to be determined with cancellation of background capacitance.

In time intervals T7 through T12, everything is the same as for the intervals T1 through T6 except that the probing electric fields and reference signal are at frequency F2 instead of at F1. It is to be understood that this method can be extended to more frequencies than two. Also, it is to be understood that in many cases, just one or the other of the real or imaginary parts of capacitance may be required. In those cases the appropriate time intervals in the drive reference signals can be eliminated and the demodulation simplified.

Referring again to FIG. 13, the detected signal D, when sampled and held by sample and hold circuits 46 at the ends of time intervals T1, T3 and T5 respectively, yields the signals S1, S2 and S3 as described earlier and presents these signals to signal processor 47 on demodulator 40 outputs 48. Details of time demultiplexing methods as outlined here are well known to those skilled in the art.

Processor 47 computes grain angle G from $G=0.5 \tan^{-1}(S2/S1)$, signal strength SS from $SS=(S1^2+S2^2)^{1/2}$, and normalized signal strength NSS from $NSS=(S1^2+S2^2)^{1/2}/S3$. These measures of grain angle, signal strength and normalized signal strength are obtained from the real part of permittivity.

Similarly, the detected signal D generated during time intervals T2, T4 and T6 yields on other demodulator 40 outputs 48, signals stemming from the imaginary part of permittivity, i.e. conductivity. These signals from the imaginary part of permittivity can be used in the same way as for the real part to obtain grain angle, signal strength and normalized signal strength based on conductivity.

Where necessary, to distinguish the results from the real and imaginary parts of permittivity, we append a letter R or I to the notation. Thus, S1R, S2R and S3R from demodulator outputs 48 can be used by processor 47 to yield GR, SSR and NSSR referring to grain angle, signal strength and normalized signal strength obtained from measures of the real part of the permittivity. Similarly, S1I, S2I and S3I from other demodulator 40 outputs 48 can be used by processor 47 to yield GI, SSI and NSSI referring to grain angle, signal strength and normalized signal strength obtained from measures of the imaginary part of the permittivity. Or, processor 47 can operate on all six of these demodulator outputs 48, in total, namely S1R, S2R, S3R, S1I, S2I, and S3I, and perhaps other demodulator outputs (other frequencies) along with outputs from auxiliary apparatus 4 to achieve a more general result.

Another version of the preferred embodiment for obtaining information at multiple frequencies can be realized by sequentially running through the frequencies before changing the direction of the probing field. In this case, consider three measurement time intervals corresponding to measurements S1, S2 and S3 each divided into subintervals. A first set of subintervals corresponds to the first frequency and consists of the first subinterval from each of the three intervals, a second set of subintervals corresponds to the second frequency and consists of the second subinterval from each of the three intervals, and so on. An electrical property of the dielectric material specimen is obtained by processing information from a corresponding set of subintervals. For example, a particular set of subintervals could yield information about the real part of the permittivity at a particular frequency.

Figure 15:
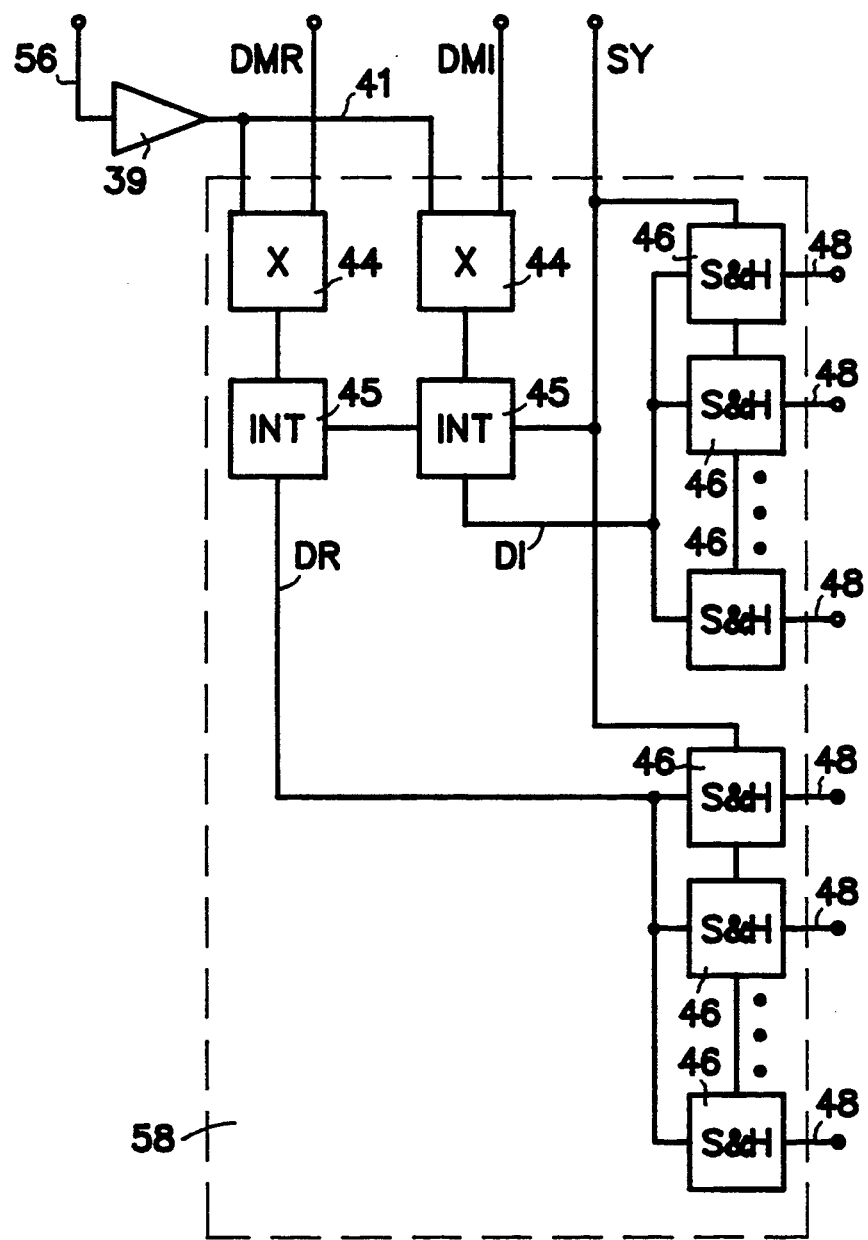
FIG. 15 illustrates a demodulator that allows some of the measuring process to be accomplished in parallel.
Figure 16:
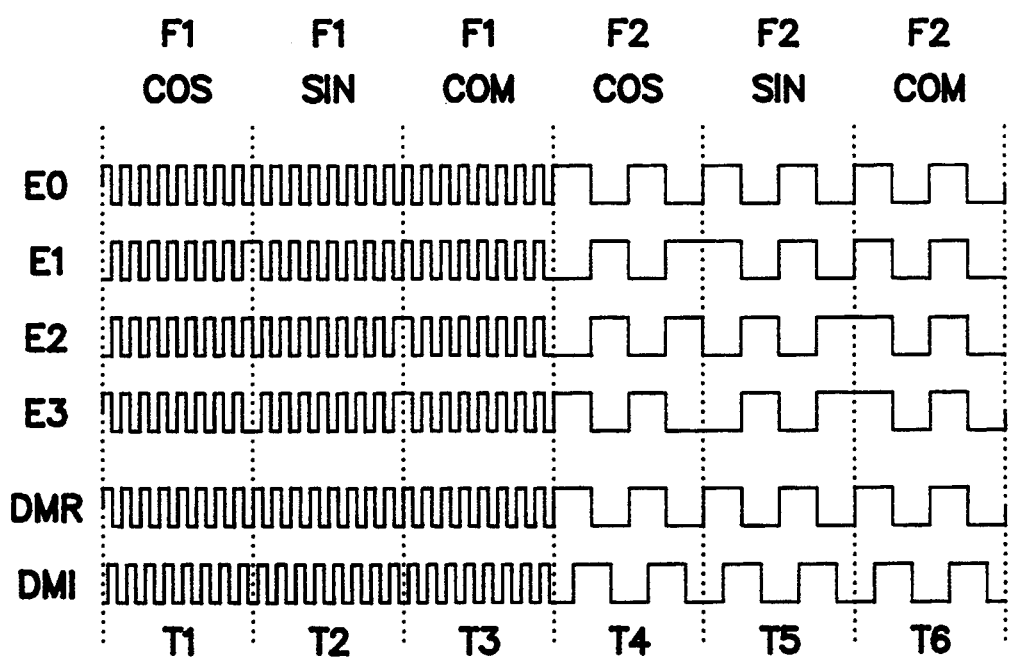
FIG. 16 illustrates drive and reference signals appropriate for use with the demodulator of FIG. 15.

Instead of obtaining the information sequentially from one multiplier/integrator combination, another version of the embodiment defines differently the time-varying electric potential signals E0, E1, E2 and E3 and applies respectively a pair of reference signals DMR and DMI to a pair of multiplier/integrators yielding integrator outputs DR and DI. This is illustrated in FIG. 15 which shows a demodulator 58 which in this case would be used in place of alemodulator 40 of FIG. 13. This would require two reference signals DMR and DMI from signal generator 38 of FIG. 13 instead of the one DM shown there. The demodulator 58 of FIG. 15 achieves simultaneous demodulation so that information about real and imaginary parts of permittivity is obtained simultaneously instead of sequentially. FIG. 16 illustrates time-varying electric potential signals and reference signals applicable for FIG. 15.

One can think of the embodiment in FIG. 13 using the sequential arrangement of FIG. 14 as obtaining information from the dielectric specimen in three sequential time intervals for the purpose of probing first in one direction, second in another direction and third equally in all directions of a plane parallel to the electrode unit's operative surface; and then repeating the process for each frequency of interest. Each interval is subdivided into two subintervals, the first to obtain the real pan and the second to obtain the imaginary part of the measurement.

The arrangement of FIG. 15 and FIG. 16 accomplishes the same objective, but instead of obtaining real and imaginary parts in sequence with sequential subintervals, the real and imaginary parts are obtained simultaneously with two channels operating in parallel. At the cost of additional demodulation apparatus, the time required to obtain the information is reduced by a factor of two. There are twice as many multipliers and integrators for demodulation in FIG. 15 as compared with FIG. 13; however, the same number of sample and hold circuits 46 are used. The array of sample and hold circuits in FIG. 13 is divided into two sub-arrays in FIG. 15. One sub-array operates on detected Signal DR to provide outputs 48 with information about the real part of permittivity, and the other operates on detected signal DI to provide other outputs 48 with information about the imaginary part of permittivity.

Figure 17:
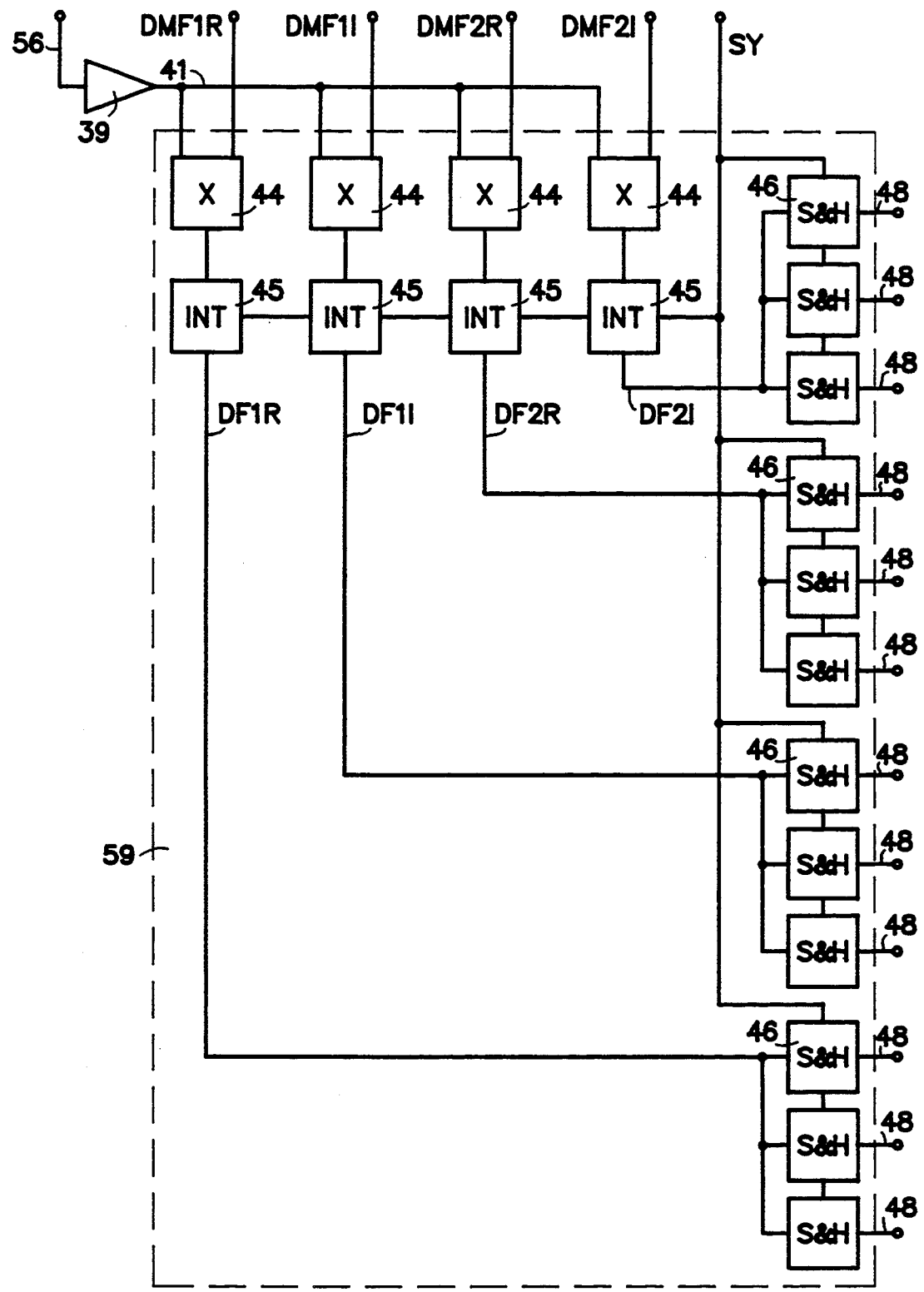
FIG. 17 illustrates a demodulator that achieves even further parallel demodulation than in FIG. 15.
Figure 18:
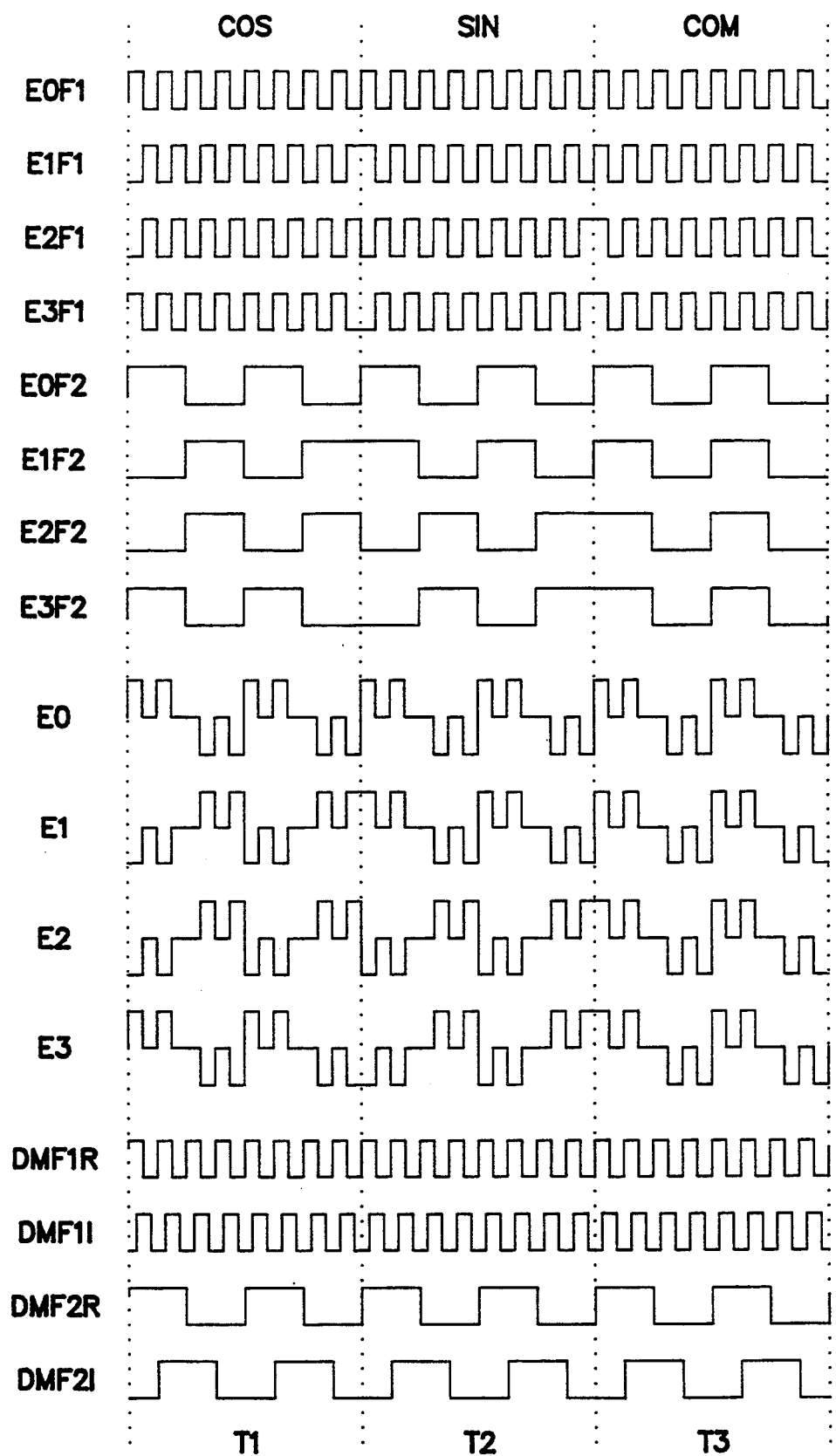
FIG. 18 illustrates drive and reference signals that can be used with the demodulator of FIG. 17.

Still further progress toward parallel detection can be achieved with another version of the preferred embodiment. FIG. 17 and FIG. 18 respectively illustrate demodulation and time-varying electric potential signals appropriate for the situation where the probing frequencies F1 and F2 are to be investigated simultaneously. In FIG. 18 the time-varying electric potential signals E0, E1, E2 and E3 are composites of signals at the probing frequencies F1 and F2. For example, the signal E0 is the sum of the signals EOF1 and EOF2 and similarly for the other signals E1, E2 and E3. Four reference signals DMF1R, DMF1I, DMF2R and DMF2I are used in four multiplier/integrator combinations to obtain simultaneously the detected signals DF1R, DF1I, DF2R and DF2I. These signals are sampled and held to give demodulator 59 outputs 48 which have information about real and imaginary parts of permittivity for frequencies F1 and F2 respectively.

FIG. 13 through FIG. 18 illustrate versions of the preferred embodiment which demonstrate how information from the dielectric sensor can be taken sequentially with a single multiplier/integrator combination or in parallel with multiple multiplier/integrators. In general, the components of each of the time-varying electric potential signals, for example the components EOF1 and EOF2 of the signal E0 in FIG. 18 should be orthogonal with respect to each other over each measurement time interval. For the preferred embodiment, one signal is orthogonal with respect to another over an interval if the integral of their product is zero over the interval. Although this restrictive definition of orthogonality is appropriate for this embodiment, it is to be understood that other more general definitions of orthogonality may be used.

The reference signals used in the preferred embodiment are each matched over measurement time intervals to components of time-varying electric potential signals to be detected during corresponding intervals. Two signals H1 and H2 are matched over an interval if $(I(H1*H2))^2/(I(H1^2)*I(H2^2))=1$, where $I(H)$ indicates integral over the interval, and * denotes multiplication. With this notation and the above definition of orthogonality, it is seen that $I(H1*H2)=0$ if and only if H1 is orthogonal to H2.

The demodulators (40, 58 and 59 respectively) illustrated in FIG. 13, FIG. 15 and FIG. 17 are shown implemented with multipliers, integrators and sample and hold circuits. Other implementations, for example matched filters, can be used for the same purpose. These details of demodulation and detection methods are well known to those skilled in the art. A multiplier we have found useful is integrated circuit analog multiplier Part No. AD734 available from Analog Devices Corporation in Norwood Mass. Amplified sense signal 41 is one input, and a reference signal, e.g. DM in FIG. 13, is the other input. The output is the product of the inputs except for a scale factor which can be adjusted by other connections to the multiplier per the manufacturer's instructions.

Methods and apparatus for generating signals such as those illustrated in FIG. 14, FIG. 16 and FIG. 18 are well known to those skilled in the art. However, additional details are available in description of preferred embodiments of the former patent.

Although the term frequency has been loosely applied to square waves, it is to be understood that any square wave has a series of sinusoidal frequency components. The term sequency has been used in the literature to refer to what has been called frequency here for members of the family of functions known as Walsh functions, and square waves are members of this family. The Walsh functions, as a complete orthogonal set of functions over a period, are definitely candidates for the time-varying electric potential signals used to drive the drive electrodes of the electrode units. No undue significance should be attached to the term frequency other than in describing that one signal varies more rapidly than another. In general, signals which can be used to define time-varying electric potentials applied to drive electrodes of the dielectric sensor can be as simple as single frequency sinusoids or they may contain multiple components at different frequencies. In this way a dielectric specimen can be investigated at a single frequency or at multiple frequencies. Or, its response to specific functions which may or may not have many different frequency components can be determined. The response to individual frequency components or to individual specific functions can be determined by using demodulators such as those described. The reference signals used are matched to components of the time-varying electric potential signals which are of interest.

Following detection, the demodulator outputs 48 are input to processor 47 together with auxiliary variable values 49 from auxiliary sensor apparatus 4.

When a plurality of electrode units are used as illustrated in FIG. 1 and FIG. 2, either separate demodulators such as 40, 58 or 59 in FIG. 13, FIG. 15 or FIG. 17 can be used or just one demodulator can be used with standard time-multiplexing and demultiplexing procedures. In this way processor 47 has access to data from a plurality of locations. Of course, by use of processor memory, the same result can be achieved with just one electrode unit used to scan the specimen sequentially.

The processor can operate in two modes under program control. In its training mode, the processor uses patterns called training patterns having known classification values (e.g. known lumber grade for each pattern) or known quantity values (e.g. known tensile strength for each pattern). In the training mode, the system determines from the training patterns a best set of features and classification boundaries.

In its feature extraction or classification mode, unknown patterns from the detected variables and auxiliary inputs are processed. Transformations identified during the training phase are used to map unknown patterns into feature space, and the results are obtained by using stored parameter values determined from the training patterns.

In some cases, outputs 61 of feature extractor 60 are sufficient; hence these outputs are shown in FIG. 13 as going directly to controlled apparatus 53 as well as to classifier 63. For example, this is the situation where linear regression is used on the data to give best least squares estimates for desired quantities such as strength or moisture content. However, in other cases where the required output is a class or category, such as a lumber grade, the classification step is required. FIG. 13 shows output 62 by itself from the classifier 63 as well as a connection of this output to the controlled apparatus 53.

Tradeoffs involving speed and amount of hardware required must be considered in the choice of approach. Because these types of choices are well known to those skilled in the art, no further description is provided here. However, it is worth pointing out that inputs to the feature extraction and classification steps can be considered independently to give multiple results from multiple electrode units, each result being applicable to regions scanned by the corresponding electrode unit. Or, the inputs to the feature extraction and classification steps can all be treated together as a single higher dimension pattern vector with results applicable to the totality of the regions scanned.

The dielectric sensor has application to wood and other anisotropic dielectric materials. Composite products such as flakeboard, laminated veneer lumber and fiberglass are examples of applications for the dielectric sensor other than naturally occurring wood that has been machined to a desired size and shape.

Flakeboard panel is a composite wood product in which wood flakes are coated with adhesive resin, laid into a mat and pressed together into the panel. Another example is laminated veneer lumber (LVL) in which veneer sheets are bonded together with the grain direction of each sheet going generally in the same direction. The resulting billets can be machined into the sizes and shapes required.

A non-wood example of a reconstituted dielectric material is fiberglass composite wherein fiberglass strands are oriented, laid into a mat, impregnated with a resin and cured.

The anisotropic character of structural dielectric materials is used to great benefit. To obtain maximum structural value from wood timbers, LVL, flakeboard, and dielectric composites, one must take into account the preferred direction of alignment and the amount of alignment.

In many plants that produce flakeboard and in vimally all new plants, there is included a means for aligning the flakes as part of the manufacturing process. Alignment of the flakes greatly improves the physical properties of the flakeboard.

As further description of the preferred embodiment, we define here two ways to use the dielectric sensor for measuring the amount of alignment in flakeboard. For illustration, in FIG. 2 assume that this plan view shows three electrode units 1 of the dielectric sensor with operative surfaces adjacent and substantially parallel to a surface of a flakeboard panel.

Signal Strength Method

At any location on the surface of a flakeboard panel, a signal strength SS or normalized signal strength NSS from any of the electrode units of the dielectric sensor can be used to indicate the amount of alignment. The signal strength method is based on an extension of the axial data computations described by Mardia, recognition that grain direction is an example of axial data, and the fact that the hardware of the dielectric sensor naturally processes the contributions from individual elements in a manner similar to Mardia's arithmetic. The process is as follows:

1. Use the dielectric sensor to obtain signal strength SS (or normalized signal strength NSS) from one of the electrode units near the flakeboard specimen. By itself SS (or NSS) can be used to indicate the amount of alignment because this measure relates to the amount of anisotropy. However, this measure can be normalized against the effect of other variables with the following additional steps.
2. Use the dielectric sensor to obtain SS (or NSS) of a uniform straight grain wood calibration block having the same moisture content, spacing between electrode unit and measured material, species and density as the flakeboard.
3. Obtain a normalized measure of amount of alignment by dividing the result from step 1 by the result from step 2. The normalization achieved by this division calibrates the alignment measurement to a specimen which is assumed to be perfectly aligned and otherwise is tested under the same conditions as the alignment block. We define percent alignment by raising this ratio to the power $\frac{1}{4}$ and multiplying by 100.

These steps disclose how to use data from one electrode unit at one location on the flakeboard panel. To scan along the trajectories 8 of FIG. 2, it is necessary to process the information and obtain results at each point scanned. To use data from each of the three electrode units shown, either multiple processors working in parallel are provided or time-multiplexing methods are used. Of course, the processor can gather in memory the results at points scanned and make an overall decision or classification of the complete panel as part of the classification step.

Angle Method

The angle method uses a plurality of measurements of grain angle from the dielectric sensor at representative locations over the surface of the flakeboard. These data could, for example, come from the three electrode units 1 of FIG. 2 at points along trajectories 8 shown in FIG. 2. The method is based on the discovery that axial data methods discussed by Mardia can be applied and is an example where data measured at a plurality of points on the flakeboard are used to provide results applicable to the whole flakeboard. The following describes the method as though the data came from just one electrode unit. However, it is to be understood that the data could equally well have come from one or a plurality of electrode units each having the same geometry.

Assume that the number of measurement points is n'. The data from these points is processed to yield grain angle at each point. The resulting n' grain angle values $G_k$, k=1,2, ..., n', are used to obtain a measure of the amount of alignment according to the following steps:

1. Define the mean vector R' in terms of its magnitude R' and the double angle 2G':

$$R' = (c'^2 + s'^2)^{\frac{1}{2}}$$

$$2G' = \tan^{-1}(s'/c')$$

where:

$$c' = \sum_{k=1}^{n'} (1/n')\cos(2G_k)$$

$$s' = \sum_{k=1}^{n'} (1/n')\sin(2G_k)$$

are the components of the vector R'. G' is taken as the general direction of alignment over a region of the material represented by the n' measurements.

2. Compute percent alignment, A, from:

$$A = 100(R')^{(n/4)}$$

where the value n is an effective number of flakes contributing to each measurement.

Percent alignment varies between 0 for randomly aligned flakes and 100 for perfectly aligned flakes wherein all flakes are aligned in the same direction. The number n is influenced by the size distribution of the flakes, the size and geometry of the electrode unit electrode array and the correlation of the flake angles. For example, if the size of the flakes is small with respect to the electrode unit's sensitive area, then n is large. If the flake angles are highly correlated, then the angle of a flake depends on the angles of other flakes. For purposes of this calculation they behave together somewhat as one larger flake; and the effective number n is reduced. In some cases where n is unknown or difficult to estimate, it can be used as a calibration parameter and adjusted until the result comes out right when the dielectric sensor is used on a calibration panel. The amount of alignment, expressed as percent alignment, A, for the calibration panel must be known from some other means, for example by using image analysis methods as described by R. Geimer, "Flake Alignment in Particleboard as Affected by Machine Variables and Particle Geometry," USDA FS Res. Pap. FPL 275, Madison Wis. 1976. Alternatively, a calibration panel can be carefully fabricated with known mount of alignment especially for this purpose.

If another process, perhaps the aligning process itself, can be developed to yield a specified amount of alignment or indicate the amount it is yielding, then the dielectric sensor can be used to estimate the effective number n which is a reciprocal measure of an "average size" of the flakes used. This estimated number n" can be computed by solving for n in the above equation defining percent alignment A. That is: n"=4(log(A)−2)/log(R'), where log is the logarithm to the base 10, and percent alignment is assumed known.

In compliance with the statute, the invention has been described in language moreover less specific as to structural features. It is to be understood, however, that the invention is not limited to the specified features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A method for obtaining a measure of the amount of anisotropy of an electrical property in a dielectric material specimen about a selected test point in a surface of the specimen, the electrical property being considered over directions in a measurement plane substantially parallel to the specimen surface at the test point, the method comprising the following steps:

applying a time-varying electric field in at least two directions in a neighborhood of the test point;

obtaining, during a first measurement time interval, a first signal proportional to the cosine of twice the angle in the measurement plane from a selected reference direction to the direction of electrical property maximum, the selected reference direction being any direction in the measurement plane;

obtaining, during a second measurement time interval, a second signal proportional to the sine of twice the angle in the measurement plane from the selected reference direction to the direction of electrical property maximum; and processing the first and second signals to obtain the measure of the amount of anisotropy, the measure being independent of the selected reference direction.

2. The method of claim 1 wherein the processing step comprises:

measuring the amount of anisotropy as the square root of the sum of the squares of the first and second signals.

3. The method of claim 1 comprising additionally the following steps:

obtaining, during a third measurement time interval, a third signal which is proportional to the isotropic component of the electrical property near the test point in directions of the measurement plane; and processing the third signal to obtain a measure of the isotropic component of the electrical property near the test point in directions of the measurement plane.

4. The method of claim 3 wherein wood is a constituent of the dielectric material specimen.

5. The method of claim 3 wherein the step of applying the time-varying electric field includes application of a time-varying electric field to substantially cancel background effect.

6. The method of claim 3 wherein the electrical property is the real part of permittivity.

7. The method of claim 3 wherein the electrical property is the imaginary part of permittivity.

8. The method of claim 3 comprising additionally the following step:

dividing the measure of the amount of anisotropy by the measure of the isotropic component to obtain a normalized measure of the amount of anisotropy.

9. The method of claim 3 wherein the steps are replicated with a different time-varying electric field being applied during each replication.

10. The method of claim 3 wherein the three measurement time intervals are divided into sets of subintervals, the first set consisting of the first subinterval from each of the three intervals, the second set consisting of the second subinterval from each of the three intervals, and so on, and the steps of obtaining the first, second and third signals are arranged so that the isotropic and anisotropic measures for a particular time-varying electric field are obtained by processing the first, second and third signals from a corresponding particular set of subintervals.

11. The method of claim 3 wherein the time-varying electric field is applied as a superposition of a plurality of time-varying electric field components which are mutually orthogonal over a time interval.

12. The method of claim 3 comprising additionally the following step:

estimating a physical property of the dielectric material specimen.

13. The method of claim 12 wherein an auxiliary variable is used in the estimation process.

14. The method of claim 13 wherein the auxiliary variable is temperature.

15. The method of claim 13 wherein the estimated physical property is moisture content.

16. The method of claim 3 comprising additionally the following step:

applying pattern recognition processing methods to categorize the dielectric material specimen into one of a plurality of categories.

17. The method of claim 16 wherein an auxiliary variable is used as input by the pattern recognition processing methods.

18. The method of claim 1 comprising additionally the following steps:

processing the first and second signals for each of a plurality of test points to obtain the angle in the measurement plane at each test point from the reference direction to the direction of electrical property maximum, the reference direction being common to all the measurement planes at the plurality of test points;

computing the average of the cosines of twice the angles at the plurality of test points;

computing the average of the sines of twice the angles at the plurality of test points; and computing a measure of the amount of alignment of the dielectric material specimen as a function of the square root of the sum of the squares of the average of the cosines and the average of the sines.

19. The method of claim 18 wherein the function is a power function.

20. The method of claim 1 comprising additionally the following steps:

processing the first and second signals for each of a plurality of test points to obtain the angle in the measurement plane at each test point from the reference direction to the direction of electrical property maximum, the reference direction being common to all the measurement planes at the plurality of test points;

computing the average of the cosines of twice the angles at the plurality of test points;

computing the average of the sines of twice the angles at the plurality of test points; and computing a measure of size of constituent elements in the dielectric material specimen as a function of the average of the cosines and the average of the sines.

* * * * *